Figure 1A:
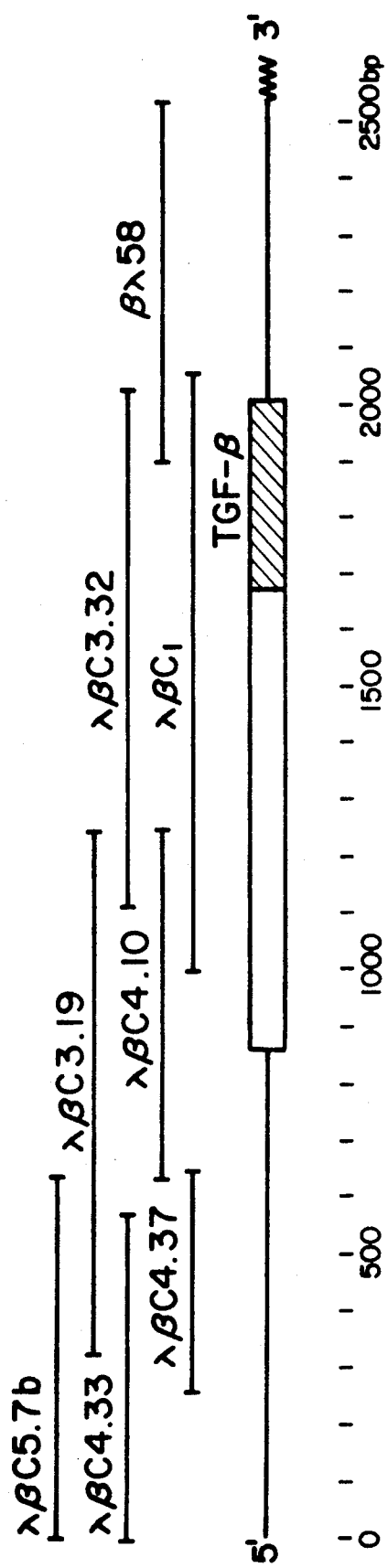

United States Patent [19]

Derynck et al.

[11] Patent Number: 5,168,051

[45] Date of Patent: * Dec. 1, 1992

[54] NUCLEIC ACID ENCODING TGF-$\beta$ ITS USES

[75] Inventors: Rik M. A. Derynck, So. San Francisco; David V. Goeddel, Hillsborough, both of Calif.

[73] Assignee: Genentech, Inc., South San Francisco, Calif.

[*] Notice: The portion of the term of this patent subsequent to Dec. 12, 2006 has been disclaimed.

[21] Appl. No.: 389,929

[22] Filed: Aug. 4, 1989

Related U.S. Application Data

[63] Continuation of Ser. No. 25,423, Mar. 13, 1987, Pat. No. 4,886,747, which is a continuation-in-part of Ser. No. 715,142, Mar. 22, 1985, abandoned.

[51] Int. Cl.$^5$ .................... C12P 21/02; C12N 15/11
[52] U.S. Cl. ................... 435/69.4; 435/69.1; 435/172.3; 435/240.2; 435/320.1; 530/27; 935/11

[58] Field of Search ............ 435/69.1, 69.4, 69.5, 435/91, 172.1, 172.3, 240.1, 240.2, 252.3–252.35; 536/27; 935/11; 530/350

[56] References Cited

U.S. PATENT DOCUMENTS 4,886,747 12/1989 Derynck et al. ............... 435/69.4

OTHER PUBLICATIONS

Ullrich et al., EMBO J., 3(2):361–364 (1984).
Massague & Like, J. Biol. Chem., 260(5):2636–2645 (1985).
Seeburg et al., Nature 270: 486 (1977).
D'Andrea et al.; Nucleic Acids Res. 9: 3119 (1981).

*Primary Examiner*—James Martinell
*Attorney, Agent, or Firm*—Janet E. Hasak

[57] ABSTRACT

Nucleic acid encoding TGF-$\beta$ has been isolated and cloned into vectors which are replicated in bacteria and expressed in eukaryotic cells. TGF-$\beta$ is recovered from transformed cultures for use in known therapeutic modalities. Nucleic acid encoding TGF-$\beta$ is useful in diagnosis and identification of TGF-$\beta$ clones.

21 Claims, 10 Drawing Sheets

Fig.1b(I)

```
                                                                                                              sstII
       sstII
  1  ACCTCCCTCC GCGGAGCAGC CAGACAGGGA GGGCCCCGGC CGGGGGCAGG GGGGACGCCC CGTCCGGGGC GCTCTGAGCC ACCCCCCCCG GCCCGCGGGG 101  CCGGCCTCGG CCCGGAGCGG AGGAAGGAGT CGCCGAGGAG CAGCCTGAGG CCCCAGAGTC TGAGACGAGC CGCCGCCGCC CCCGCCACTG CGGGGAGGAG 201  GGGGAGGAGG AGCGGGAGGA GGGACGAGCT GGTCGGGAGA AGAGGAAAAA AACTTTTGAG ACTTTTCCGT TGCCGCTGGG AGCCGGAGGC GCGGGGACCT 301  CTTGGCGCGA CGCTGCCCCG CGAGGAGGCA GGACTTGGGG ACCCCAGACC GCCTCCCTTT GCCGCCGGGG ACGCTTGCTC CCTCCCTGCC CCCTACACGG 401  CGTCCCCTCAG GCGCCCCCAT TCCGGACCAG CCCTCGGGAG TCGCCGACCC GGCCTCCCGC AAAGACTTTT CCCCAGACCT CGGGGCGCACC CCCTGCACGC kpnI
501  CGCCTTCATC CCCGGCCTGT CTCCTGAGCC CCCGGCCATC CTAGACCCTT TCTCCTCCAG GAGACGGATC TCTCTCCGAC CTGCCACAGA TCCCCTATTC 601  AAGACCACCC ACCTTCTGGT ACCAGATCGC GCCCATCTAG GTTATTTCCG TGGGATACTG AGACACCCCC GGTCCAAGCC TCCCCTCCAC CACTGCGCCC pstI
701  TTCTCCCTGA GGAGCCTCAG CTTTCCCTCG AGGCCCTCCT ACCTTTTGCC GGGAGACCCC CAGCCCCTGC AGGGGCGGGG CCTCCCCACC ACACCAGCCC 1
                                                                               Met Pro Pro Ser Gly Leu Arg Leu Leu Pro Leu Leu Leu Pro Leu Leu
801  TGTTGCGCT  CTCGGCAGTG CCGGGGGGCG CCGCCTCCCC C ATG CCG CCC TCC GGG CTC CGG CTG CTG CCG CTG CTG CTA CCG CTG
                                                                                                              11
```

Fig. 1b (II)

```
                    21                                  sstII    31                                          41
        Trp Leu Val Leu Thr Pro Gly Pro Pro Ala Ala Gly Leu Ser Thr Cys Lys Thr Ile Asp Met Glu Leu Val Lys Arg
 890    TGG CTA GTG CTG ACG CCT GGC CCG CCG GCC GCG GGA CTA TCC ACC TGC AAG ACT ATC GAC ATG GAG CTG GTG AAG CGG sstII  51                                  61
        Lys Arg Ile Glu Ala Ile Arg Gly Gln Ile Leu Ser Lys Leu Arg Leu Ala Ser Pro Pro Ser Gln Gly Glu Val Pro Pro
 971    AAG CGC ATC GAG GCC ATC CGC GGG CAG ATC CTG TCC AAG CTG CGG CTC GCC AGC CCG CCG AGC CAG GGG GAG GTG CCG CCC 71                                          81                                          91
        Gly Pro Leu Pro Glu Ala Val Leu Ala Leu Tyr Asn Ser Thr Arg Asp Arg Val Ala Gly Glu Ser Ala Glu Pro Glu Pro
1052    GGC CCG CTG·CCC GAG GCC GTG CTC GCC CTG TAC AAC AGC ACC CGC GAC CGG GTG GCC GGG GAG AGT GCA GAA CCG GAG CCC 101                                         111                                         121
        Glu Pro Glu Ala Asp Tyr Tyr Ala Lys Glu Val Thr Arg Val Leu Met Val Glu Thr His Asn Glu Ile Tyr Asp Lys Phe
1133    GAG CCT GAG GCC GAC TAC TAC GCC AAG GAG GTC ACC CGC GTG CTA ATG GTG GAA ACC CAC AAC GAA ATC TAT GAC AAG TTC 131                                         141    kpnI                                 151
        Lys Gln Ser Thr His Ser Ile Tyr Met Phe Phe Asn Thr Ser Glu Leu Arg Glu Ala Val Pro Glu Pro Val Leu Leu Ser
1214    AAG CAG AGT ACA CAC AGC ATA TAT ATG TTC TTC AAC ACA TCA GAG CTC CGA GAG GCG GTA CCT GAA CCC GTG TTG CTC TCC 161                                         171
        smaI
        Arg Ala Glu Leu Arg Leu Leu Arg Leu Lys Leu Lys Val Glu Gln His Val Glu Leu Tyr Gln Lys Tyr Ser Asn Asn Ser
1295    CGG GCA GAG CTG CGT CTG CTG AGG CTC AAG TTA AAA GTG GAG CAG CAC GTG GAG CTG TAC CAG AAA TAC AGC AAC AAT TCC 181                                         191                                         201
        Trp Arg Tyr Leu Ser Asn Arg Leu Leu Ala Pro Ser Asp Ser Pro Glu Trp Leu Ser Phe Asp Val Thr Gly Val Val Arg
1376    TGG CGA TAC CTC AGC AAC CGG CTG CTG GCA CCC AGC GAC TCG CCA GAG TGG TTA TCT TTT GAT GTC ACC GGA GTT GTG CGG 211                                         221                                         231
        Gln Trp Leu Ser Arg Gly Gly Glu Ile Glu Gly Phe Arg Leu Ser Ala His Cys Ser Cys Asp Ser Arg Asp Asn Thr Leu
1457    CAG TGG CTG AGC CGT GGA GGG GAA ATT GAG GGC TTT CGC CTT AGC GCC CAC TGC TCC TGT GAC AGC AGG GAT AAC ACA CTG 241                                         251
        Gln Val Asp Ile Asn Gly Phe Thr Thr Gly Arg Arg Gly Asp Leu Ala Thr Ile His Gly Met Asn Arg Pro Phe Leu Leu
1538    CAA GTG GAC ATC AAC GGG TTC ACT ACC CGC CGA GGT GAC CTG GCC ACC ATT CAT GGC ATG AAC CGG CCT TTC CTG CTT
```

Fig. 1b(III)

```
         261                      271                      281
     Leu Met Ala Thr Pro Leu Glu Arg Ala Gln His Leu Gln Ser Ser Arg His Arg Arg Ala Leu Asp Thr Asn Tyr Cys Phe
1619 CTC ATG GCC ACC CCG CTG GAG AGG GCC CAG CAT CTG CAA AGC TCC CGG CAC CGC CGA GCC CTG GAC ACC AAC TAT TGC TTC
                                                                                                  311 bamHI
         291                      301                      311
     Ser Ser Thr Glu Lys Asn Cys Cys Val Arg Gln Leu Tyr Ile Asp Phe Arg Lys Asp Leu Gly Trp Lys Trp Ile His Glu
1700 AGC TCC ACG GAG AAG AAC TGC TGC GTG AGG CAG CTG TAC ATT GAC TTC CGC AAG GAC CTC GGC TGG AAG TGG ATC CAC GAG 321                      331
     Pro Lys Gly Tyr His Ala Asn Phe Cys Leu Gly Pro Cys Pro Tyr Ile Trp Ser Leu Asp Thr Gln Tyr Ser Lys Val Leu
1781 CCC AAG GGC TAC CAT GCC AAC TTC TGC CTC GGG CCC TGC CCC TAC ATT TGG AGC CTG GAC ACG CAG TAC AGC AAG GTC CTG
         341                              smaI             351                      361
     Ala Leu Tyr Asn Gln His Asn Pro Gly Ala Ser Ala Ala Pro Cys Cys Val Pro Gln Ala Leu Glu Pro Leu Pro Ile Val
1862 GCC CTG TAC AAC CAG CAT AAC CCG GGC GCG TCG GCG GCG CCG TGC TGC GTG CCG CAG GCG CTG GAG CCG CTC CCC ATC GTG
         371                      381
     Tyr Tyr Val Gly Arg Lys Pro Lys Val Glu Gln Leu Ser Asn Met Ile Val Arg Ser Cys Lys Cys Ser
1943 TAC TAC GTG GGC CGC AAG CCC AAG GTG GAG CAG CTG TCC AAC ATG ATC GTG CGC TCC TGC AAG TGC AGC TGA
                                                                                                  ncoI
2018 CCCGCCCCGC CCCGCCCCGC CCCGGCAGGC CCGGCCCCAC CCCGCCCCGC TTGCCCATGG GGGCTGTATT TAAGGACACC GTGCCCCAAG
2118 CCCACCTGGG GCCCCATTAA AGATGGAGAG AGGACTGCGG ATCTCTGTGT CATTGGGCGC CTGCCTGGGG TCTCCATCCC TGACGTTCCC CCACTCCCAC
                                                                                                  bglII
2218 TCCCTCTCTC TCCCTCTCTG CCTCCTCCTG CCTGTCTGCA CTATTCCTTT GCCCGGCATC AAGGCACAGG GGACCAGTGG GGAACACTAC TGTAGTTAGA
2318 TCTATTATT GAGCACCTTG GGCACTGTTG AAGTGCCTTA CATTAATGAA CTCATTCAGT CACCATAGCA ACACTCTGAG ATGGCAGGGA CTCTGATAAC
2418 ACCCATTTTA AAGTTGAGG AAACAAGCCC AGAGAGGTTA AGGAGGAGT TCCTGCCCAC CAGGAACCTG CTTTAGTGGG GGATAGTGAA GAAGACAATA
2518 AAAGATAGTA GTTCAGGCCA
```

Fig.2.

```
  1 GATCAGTTTA CATGGAGCTG TGTTATTTTG TATGTTCCAG GGTGTGGCAT GCCATGATTT ATTTAGCCCC CCGTGGATG GTCATCTGGC TTCTTACAGG

101 CTTGTCTTAA GCATTGCGTG AAATTAATTA TTACATTGCT CTTAGCACTG GAGGAAGTGC TTAATCTGTG TTAGTGATTA TCATGACTAT TTGTGTTGTT

201 ATTAACACAG TGGGTGCAAG GGAGACCCAG ATGGAGATAG GGCTGGGGGG GCAACCTAGG GTGACACACG CACCTGGGGA GGAGGGGCAT GTGGCTTCTA
                                                                                                    252
                                                                                                     r Ser Thr Glu Lys Asn Cys Cys Val Arg Gln Leu Tyr Ile Asp
                                                                                                                                                        261
301 TGGTGGTAGC CCCTCCCTGC CCCTGATGCG TCTCTCCTGC CTGCAG      C TCC ACG GAG AAG AAC TGC TGC GTG CGG CAG CTG TAC ATT GAC
                                           bamHI      281
                    271              Phe Arg Lys Asp Leu Gly Trp Lys Gly Tyr Ile His Glu Pro Lys Gly Tyr His Ala Asn Phe Cys Leu Gly Pro Cys Pro Tyr
390                                  TTC CGC AAG GAC CTC GGC TGG AAG GGC TAC ATC CAC GAG CCC AAG GGC TAC CAT GCC AAC TTC TGC CTC GGG CCC TGC CCC TAC
                                                           301
                                     Ile Trp Ser Leu Asp Thr Gln Tyr Ser Lys
471                                  ATT TGG AGC CTG GAC ACG CAG TAC AGC AAG   GTACGTCTGG CCACCGGGCT ACGAGATGCG CTTGGGGGGA GCCAGGACGG AGGAAGAGGA GA 563 GAGAAAGA GAAGAGGGGCT CTGAGCAGGG AGTTGGCAGG ATGGGGAGAA AGAGAGGGAT GAAGACCCAC AGAGTGAAGT AACAGAGGGA TAAAGAGATG GGGAGAGAGG C 662 AGGAAGCTA GAGAGGGGCT CTGAGCAGGG GCCAGAGGGA AAAACGCAGA AATGGAGAGA CAAAATGAGA GAGACAGATA GAAGACCAGA GTTAGGCCAA TGGGGGTGAA GGGGAGAAGA G 762 AGACAGGGA AGGAAGGA AAAACGCAGA AATGGAGAGA GATGAGGAGG GACAGAGACT GAGAAAGAAA ATCAGGCGGG CGCGGCGGCT CACGATGGTA ATACCAACAC TTTGGGACGC A 862 CAACAAGGC AAGAGGGGAA GATGAGGAGG GACAGAGACT GAGAAAGAAA ATCAGGCGGG CGCGGCGGCT CACGATGGTA ATACCAACAC TTTGGGACGC T

962 GAAGCAGGA GGATC
``` h.β-TGF₁:    ALDTNYCFSSTEKNCCVRQLYIDFRKDLGWK-WIHEPKGY
h.β-TGF₃:    ALDTNYCFRNLEENCCVRPLYIDFRQDLGWK-WVHEPKGY
p.β-TGF₃:    ALDTNYCFRNLEENCCVRPLYIDFRQDLGWK-WVHEPKGY
b.β-TGF₂:    ALDAAYCFRRVQDNCCLRPLYIDFKRDLGW----------
             *         *         *         *
             1         10        20        30 h.β-TGF₁:    HANFCLGPCPYIWSLDT----QYSKVLAL-YNQ--HNPGA
h.β-TGF₃:    YANFCSGPCPYLRSADT----THSTVLGL-YNT--LNPEA
p.β-TGF₃:    YANFCSGPCPYLRSADT----THSSVLGL-YNT--LNPEA
b.β-TGF₂:
             *         *         *         *
             40        50        60        70 h.β-TGF₁:    SAAPCCVPQALEPLPIVYYV-GRKPKVEQLSNMIVRSCKCS
h.β-TGF₃:    SASPCCMPQDLEPLTILYYV-GRTPKVEQLSNMVVKSCKCS
p.β-TGF₃:    SASPCCVPQDLEPLTILYYV-GRTAKVEQLSNMVVKSCKCS
b.β-TGF₂:
             *         *         *         *
             80        90        100       110

```
10+11.3                                                        MHLLAKPQ
                    10        20        30        40        50

10+11.3    SSGSREAAWFSSLLLHVGWGLLLTRPRSPRASLPGSRMKMHLQRALVVLA
               60        70        80        90        100

10+11.3    LLNPATVSLSMSTCTTLDFDHIKRKRVEAIPGQILSKLRLTSPPDPSMLA
              110       120       130       140       150

10+11.3    NIPTQVLDLYMSTRELLEEVHGERGDDCTQENTESEYYAKEIYKFDMIQG
              160       170       180       190       200

10+11.3    LEEHNDLAVCPKGITSKIFRFNVSSVEKNETNLFRAEFRVLRMPNPSSKR
              210       220       230       240       250 hu4                                                       CQWLL
                                                          ***
10+11.3    SEQRIELFQILQPDEHIAKQRYIDGKNLPTRGAAEWLSFDVTDTVREWLL
              260       270       280       290       300

10        20        30        40        50
hu4        RRESNLGLEISTHCPCHTFQPNGDILENIHEVMEIKFKGVDNEDDHGRGD
           ************************ *********** *** *** ****
10+11.3    RRESNLGLEISTHCPCHTFQPNGDILENIQEVMEIKFKGVDSEDDPGRGD
              310       320       330       340       350

60        70        80        90        100
hu4        LGRLKKQKDHHNPHLILMMIPPHRLDNPGQGGQRKKRALDTNYCFRNLEE
           ****** *  * ********* ****** * ** *******************
10+11.3    LGRLKKKKE-HSPHLILMMIPPDRLDNPGLGAQRKKRALDTNYCFRNLEE
              360       370       380       390

110       120       130       140       150
hu4        NCCVRPLYIDFRQDLGWKWVHEPKGYYANFCSGPCPYLRSADTTHSTVLG
           ************************************************ ***
10+11.3    NCCVRPLYIDFRQDLGWKWVHEPKGYYANFCSGPCPYLRSADTTHSSVLG
              400       410       420       430       440

160       170       180       190       200
hu4        LYNTLNPEASASPCCMPQDLEPLTILYYVGRTPKVEQLSNMVVKSCKCS
           ************** *************** ******************
10+11.3    LYNTLNPEASASPCCVPQDLEPLTILYYVGRTAKVEQLSNMVVKSCKCS
              450       460       470       480       490
```

FIG. 5

NUCLEIC ACID ENCODING TGF-β ITS USES

This is a continuation of application Ser. No. 07/025,423 filed on Mar. 13, 1987 and issued as U.S. Pat. No. 4,886,747, which is a continuation-in-part application of application Ser. NO. 06/715,142 filed Mar. 22, 1985, now abandoned.

Peptides which can induce the reversible phenotypic transformation of mammalian cells in culture have been given the name transforming growth factor (TGF)[1,2]. Type α TGF competes with epidermal growth factor (EGF) for binding to the same cell surface receptor[3]. A 50 amino acid TGF-α species has been purified and shown to share sequence homology with EGF[4]. TGF-α is synthesized by various transformed cell lines[3,5,6,91]. The 50 amino acid TGF-α is initially synthesized as part of a 160 amino acid precursor molecule which undergoes N- and C-terminal proteolytic processing to yield the mature peptide[7,8]. The detection of TGF-α species with apparently higher molecular weights[1,2,9] might be due to variable processing of the 160 amino acid precursor[92].

Type β TGF activity has been isolated from tumor cells as well as many normal tissues[10,11], including kidney[12], placenta[13] and blood platelets[14,15]. TGF-β is present in platelets, which also contain platelet-derived growth factor (PDGF) and an EGF-like peptide[16]. Bovine TGF-β has been demonstrated to accelerate wound healing in rats[17] and to induce fetal RMM cells to undergo differentiation and synthesize cartilage-specific macromolecules[80]. Treatment of NRK fibroblasts with TGF-β does, however, result in an increase in the number of membrane receptors for EGF[20]. This observation is in agreement with the known ability of TGFβ to greatly potentiate the activity of EGF and TGF-α on these cells[10,11]. Moreover TGF-β alone can induce AKR-2B fibroblasts to form colonies in soft agar[21]. Elevated levels of TGF-β are secreted by some transformed cells[22]. In addition to its ability to stimulate cell proliferation, TGF-β has been demonstrated to inhibit the anchorage-dependent growth of a variety of human cancer cell lines[13]. It is now thought that TGF-β may be identical or very similar to a growth inhibitor isolated from African green monkey (BSC-1) cells[24]. Whether TGF-β acts to stimulate or inhibit the growth of a particular cell line type appears to depend on many variables, including the physiological condition of the cell and the presence of additional growth factors.

Bovine TGF-β has been purified to sequenceable grade (U.S. Ser. No. 500,833, filed Jun. 3, 1983 abandoned). The first 15 amino-terminal residues of the mature protein were found to be Ala-Leu-Asp-Thr-Asn-Tyr-CMC-Phe-Ser-Ser-Thr-Gly-Lys-Asn-CMC-, wherein CMC is S-carboxymethyl cysteine representing cysteine or half-cystine residues.

Human TGF-β from human placenta and platelets has been purified to the same degree (respectively, U.S. Ser. No. 500,927 and 500,832, both filed Jun. 3, 1983 and now abandoned) Placental TGF-β was reported to have the following amino terminal sequence: Ala-Leu-Asp-Thr-Asn-Tyr-CMC-Phe-(Ser-Ser)-Thr-Glu-Lys-Asn-CMC-Val-X-Gln-Leu-Tyr-Ile-Asp-Phe-X-(Lys)-Asp-Leu-Gly-, wherein X was undetermined and CMC is as defined above. Platelet TGF-β was reported as the amino terminal sequence Ala-Leu-Asp-Thr-Asn-Tyr-X-Phe-Ser-, wherein CMC and X are as defined above.

Human TGF-β was reported to be composed of two polypeptide chains of very similar molecular weight ($M_r = 12,500$) which are maintained in covalent association by disulfide bonds. The disulfide bonds were considered likely to play an important role in conferring structure on the TGF-β molecule (U.S. Ser. No. 500,832).

Several other factors have been described that are related to TGF-β by limited amino acid sequence homology. The inhibin A and B beta chains are related to TGF-β by the placement of homologous cysteine residues and other limited amino acid sequence homology, from which it has been inferred that inhibin, or more accurately activin (dimers of the inhibin $beta_A$ or $beta_B$ chains). is structurally related to TGF-β. Inhibin represses the release of FSH from the pituitary, while activin enhances the release of FSH[81,82]. TGF-β is not known to have this activity.

Mullerian inhibitory substance has a C-terminal region which is homologous with TGF-β and inhibits the growth of Mullerian-derived tumors[83,84].

TGF-β prepared by purification from biological materials presents a risk of contamination by infectious agents such as HTLV-III or hepatitis viruses. Accordingly, it is an object of this invention to prepare TGF-β from sources that do not present a risk of contamination.

It is another object to prepare nucleic acid that will hybridize with DNA encoding biologically active TGF-β. When appropriately labelled, this nucleic acid is useful in diagnostic assays for TGF-β mRNA and in isolating DNA encoding TGF-β.

It is a further object herein to prepare vectors containing DNA that encodes TGF-β, together with host cell transformants that express biologically active TGF-β.

SUMMARY

In accordance with this invention, the foregoing objects are achieved by a method comprising (a) constructing a vector which includes nucleic acid encoding TGF-β, (b) transforming a heterologous host eukaryotic cell with the vector, (c) culturing the transformed cell, and (d) recovering TGF-β from the culture.

Nucleic acid encoding two subtypes of TGF-β (TGF-β1 and TGF-β3) is provided which is useful in constructing the above vectors. This nucleic acid or a nucleic acid capable of hybridizing therewith also is labelled and used in diagnostic assays for DNA or mRNA encoding TGF-β or related proteins.

The preparation of TGF-β derivatives by recombinant methods is made possible by knowledge of the TGF-β coding sequences disclosed herein. These derivatives include silent and expressed mutants in the nucleic acid encoding TGF-β.

Silent variants involve the substitution of one degenerate codon for another where both codons code for the same amino acid, but which substitution could exert a salutary effect on TGF-β yield in recombinant culture, e.g. by modifying in the secondary structure of TGF-β mRNA. and which salutary substitution is identified by screening TGF-β yields from transformants.

Expressed TGF-β variants fall into one or more of three classes: deletions, substitutions or insertions. Deletions are characterized by the elimination of amino acid residues without the insertion of a replacement residue. Deletional variants of TGF-β are useful in making TGF-β fragments, for example, where it is desired to delete an immune epitope.

Substitution variants are those in which one amino acid residue has been replaced by another. Such variants are extremely difficult to make by methods other than recombinant synthesis, especially substitutions targeted for the interior of the primary amino acid sequence. They are useful in modifying the biological activity of TGF-$\beta$. Substitution variants include allelic forms of TGF-$\beta$ as well as TGF-$\beta$ subtypes.

TGF-$\beta$ is found as a disulfide linked dimer. Further variants include heterodimers of TGF-$\beta$ subtypes and heterodimers of one TGF-$\beta$ chain having a native amino acid sequence disulfide bonded through the ordinary homodimer disulfide linkages to a predetermined variant of TGF-$\beta$. In this case, such variants include biologically active as well as biologically inactive TGF-$\beta$.

Insertional variants are those in which one or more residues are placed within the internal TGF-$\beta$ sequence or at either end thereof. Variants of this class include fusion proteins resulting from insertions at the carboxyl or amino terminal residues of TGF-$\beta$. TGF-$\beta$ fusions with bacterial or other immunogenic proteins are useful for raising antibodies against TGF-$\beta$ or its predetermined fragments.

BRIEF DESCRIPTION OF THE DRAWINGS

FIG. 1*a* is a schematic diagram of the TGF-$\beta_1$ mRNA showing the boxed coding sequence. The 112 amino acid TGF-$\beta_1$ (dashed) is encoded by the 3′ end of the coding sequence. The sequenced cDNA inserts of λβC1, 3.19, 3.32, 4.10, 4.33, 4.37 and 5 7b (described infra) and the genomic DNA sequence for the 3′ untranslated region are aligned above the diagram.

FIGS. 1*b*(I)–1*b*(III) (hereinafter referred to collectively as FIG. 1*b*) depict the sequence and deduced amino acid sequence of the preTGF-$\beta_1$ cDNA, determined from the several overlapping cDNAs and the genomic 3′ region. The 5′ terminal region which could be folded into stable hairpin loops is underlined. The preTGF-$\beta_1$ cDNA encodes a 390 amino acid protein, of which the C-terminal 112 amino acids (boxed) encode mature TGF-$62_1$. A hydrophobic domain found at the N-terminus of the precursor is overlined. An overlined Arg-Arg dipeptide precedes the proteolytic cleavage site for release of TGF-$\beta_1$. Three potential N-glycosylation sites in preTGF-$\beta_1$ are overlined. The stop codon is followed by the underlined G-C rich sequence and a downstream TATA-like sequence.

FIG. 2 depicts a genomic fragment encoding a TGF-$\beta_1$ exon and its deduced amino acid sequence Arrows show the mRNA processing sites (intron-exon junctions). The residue numbers correspond to FIG. 1*b*.

FIG. 3 is a comparison between the known N-terminal sequence of bovine TGF-$\beta_2$ and the mature human TGF-$\beta_1$ and human and porcine TGF-$\beta_3$ amino acid sequences. Unconserved substitutions in TGF-$\beta_1$ which constitute the TGF-$\beta_2$ and $\beta_3$ subtypes are designated by dots above the unconserved residues. The amino acid residue numbers shown in this Figure shall be used herein unless otherwise indicated.

FIGS. 4*a*–4*c* show the cDNA sequences for human and porcine TGF-$\beta_3$. The sequence for the human cDNA encodes a portion of the presequence region and all of the mature sequence. The human and porcine sequences are adjacent to the lines designated hu4 and 10+11.3, respectively. Gaps are introduced into the sequences in order to maximize nucleotide homology. Homologous bases are designated with an asterisk.

FIG. 5 depicts the amino acid sequences encoded by the cDNAs of FIGS. 4*a*–4*c*. Homologous residues are designated with an asterisk. Candidate translational start methionyl residues for the porcine sequence are located at positions 43, 88 or 90 (boxed methionyl residues). The C-terminal residue for both the human and porcine sequences is the seryl at 499 (porcine) or 204 (human).

DETAILED DESCRIPTION

TGF-$\beta$ has proven to be extremely difficult to synthesize in recombinant cell culture while retaining its growth-altering activity. As can be seen from FIGS. 1*b*, 3 and 5, the mature TGF-$\beta$ amino acid sequence contains a large number of cysteine residues[9], at least some of which apparently are involved in interchain cross-linking in forming the homodimeric TGF-$\beta$ which is recovered from natural sources. Furthermore, TGF-$\beta$ is expressed as a precursor molecule having a large amino terminal region not containing the recognizable $NH_2$-terminal signal peptide sequence typical of most secreted proteins, even though TGF-$\beta$ normally appears to some degree in the extracellular medium. However, eukaryotic cells have been transformed to express heterologous TGF-$\beta$, notwithstanding the anticipated difficulty in properly processing the primary translation product in recombinant culture.

This invention is directed to recombinant synthesis of TGF-$\beta$, which is defined as inclusive of biologically active preTGF-$\beta$ having the FIG. 1*b* sequence, mature TGF-$\beta$, polypeptide fragments thereof and insertion, substitution and/or deletion variants of such preTGF-$\beta$ (including alleles or other TGF-$\beta$ subtypes than the TGF-$\beta_1$ subtype shown in FIG. 1*b*). mature TGF-$\beta$ or polypeptide fragments.

Biologically active TGF-$\beta$ is defined as being capable of inducing EGF-potentiated anchorage independent growth of target cell lines[81] and/or growth inhibition of neoplastic cell lines[23]. Anchorage independent growth refers to the ability of TGF-$\beta$ and EGF treated non-neoplastic target cells to form colonies in soft agar, a characteristic ascribed to transformation of the cells (hence the name transforming growth factor). This is not to say that TGF-$\beta$ will "cause" cancer because it is now known that many normal cells express TGF-$\beta$ Paradoxically, TGF-$\beta$ also is known to inhibit the growth of several normal cell types and various neoplastic cells such as A549.

Biological activity for the purposes herein also generally includes the ability to cross-react with antisera raised against native TGF-$\beta$. Native TGF-$\beta$ is that which is obtained from platelets or other natural sources. Immunological cross-reactivity is a measure of a single active epitope and not necessarily of active TGF-$\beta$ domains involved in inducing anchorage-independent growth of target cells. However, immunologically cross-reactive proteins per se are not biologically active as defined herein unless they also exert growth-affecting activity, i.e., all biologically active TGF-$\beta$ variants promote growth in the defined assays, but not all immunologically cross-reactive TGF-$\beta$s are biologically active of course, TGF-$\beta$ which is capable of inducing anchorage independent growth frequently will exhibit immunological cross-reactivity with antisera raised against the native molecule as a corollary to maintenance of proper conformation.

The FIG. 1b nucleotide sequence was obtained by an analysis of several overlapping cDNAs and gene fragments, leading to the determination of a continuous sequence corresponding to the TGF-$\beta_1$ precursor mRNA. According to FIG. 1b an initiator ATG is located 841 nucleotides from the 5' end and establishes a coding sequence for a 390 residue polypeptide. Several areas within the cDNA sequence have an exceptionally high G-C content. The initiator ATG is flanked by two G-C rich areas of approximately 200 bp each. In addition, several regions of the cDNA, particularly the 5'-terminus, have regions with greater than 80 percent G-C content. The location of these G-C rich regions coincides with the areas in which the many cDNA cloning artifacts occurred and where partial length cDNAs were obtained.

The 5' untranslated region of the TGF-$\circ_1$ mRNA is 841 nucleotides long (assuming the ATG is located at nucleotide 842) and contains a long sequence consisting almost exclusively of purines. The biological relevance of this exceptionally long 5' untranslated region of high G-C content is unknown, but it is similar to the structural organization of c-myc mRNA. However, there is no striking sequence homology between these two sequences. The long 5' untranslated region of c-myc has been hypothesized to have a functional significance[37]. The G-C rich 5'-proximal part of the 5' untranslated sequence of human c-myc mRNA has several regions which could form stable hairpin loops. Likewise, the first 120 bp of the untranslated preTGF-$\beta_1$ cDNA can theoretically be folded into hairpin loop structures with a calculated stability of $-91$ kcal. The long 5' untranslated sequence and the potentially stable hairpin loop structures could play a role in the mRNA stability or in the regulation of transcription. Accordingly, this region can be deleted and substituted for by other 5' untranslated sequences, e.g. from viral proteins, in order to identify structures that may improve TGF-$\beta_1$ yields from recombinant cell culture.

The stop codon preceding base 2015 is immediately followed by a remarkable, G-C rich sequence of 75 nucleotides (underlined in FIG. 1b). This sequence consists of multiple repeats of CCGCC. The peculiar nature of this sequence is probably responsible for the fact that the 3' untranslated end of the mRNA could not be cloned as a cDNA sequence, perhaps due to the inability of the E. coli DNA polymerase I to use this sequence as a template for the second strand cDNA synthesis Repeat sequences of a similar nature have been found in the promoter regions of the genes for human dihydrofolate reductase[38], human transferrin receptor, human adenosine deaminase[39], and Herpesvirus thymidine kinase[40]. In the latter case, McKnight et al.[40] have shown that these structural elements are of major importance for the transcription efficiency. In addition, it has been shown that the promoter specific transcriptional factor Sp1 binds to such sequences in the SV40 early promoter region and in a related monkey promoter[41,42]. In all of these cases the G-C rich repeats are followed closely by the Goldberg-Hogness TATA sequence. In the case of preTGF-$\beta_1$, however, these sequences are located in the 3' untranslated region of the gene, but are interestingly also followed by a TATA-like sequence. No evidence that this region could function as a promoter is available. The preTGF-$\beta_1$ gene sequence has the hexanucleotide AATAAA about 500 nucleotides downstream from the stop codon. This sequence, which usually precedes the site of polyadenylation by 11 to 30 bases[32], probably functions as the preTGF-$\beta_1$ mRNA polyadenylation signal, since this would be in agreement with the size of preTGF-$\beta$ mRNA estimated from Northern hybridizations, and since 3' untranslated regions rarely contain intervening sequences. Benoist et al.[43] have proposed a consensus sequence TTCACTGC which follows the AATAAA closely and immediately precedes the polyA-tail. A similar sequence, TTCAGGCC, follows the AATAAA sequence in the 3' untranslated region of the preTGF-$\beta_1$ mRNA, providing further support for the assignment of the polyadenylation site at position 2530 (FIG. 1b).

PreTGF-$\beta_1$ is a polypeptide of 390 amino acids. Comparison of this sequence with the previously determined NH$_2$-terminus of mature TGF-$\beta_1$ shows that TGF-$\beta_1$ constitutes the C-terminal 112 amino acids of preTGF-$\beta_1$. The mature TGF-$\beta_1$ monomer is cleaved from the precursor at the Arg-Arg dipeptide immediately preceding the mature TGF-$\beta_1$ NH$_2$-terminus. A similar dibasic cleavage site is located immediately upstream from the mature TGF-$\beta_3$ amino terminus. Such proteolytic cleavage sites have been found in several other polypeptide precursor sequences, including preproenkephalin[44,45], the calcitonin precursor[46], and corticotropin-$\beta$-lipotropin precursor[47]. Determination of the hydrophobicity profile by the method of Kyte and Doolittle[48] predicts that the Arg-Arg sequence is located within a hydrophilic region which would make it accessible to a trypsin-like peptidase. Post-translational cleavage of the precursor gives rise to the mature TGF-$\beta$ monomer. The disposition of the presequence is not known but may give rise to other biologically active peptides. The TGF-$\beta_1$ and TGF-$\beta_3$ precursors contain several pairs of basic residues (FIGS. 1b and 5) which could also undergo post-translation cleavage and give rise to separate polypeptide entities. Mature TGF-$\beta_1$ contains two Arg-Lys dipeptides which apparently are not cleaved. As shown in FIG. 1b, the preTGF-$\beta_1$ precursor contains three potential N-glycosylation sites, Asn-X-Ser or Thr (FIG. 1b). None of these are localized within mature TGF-$\beta_1$. Accordingly, a method is provided whereby mature TGF-$\beta$ is purified free of glycoproteins by adsorbing the glycoproteins on immobilized lectins and eluting TGF-$\beta$ with the unadsorbed fraction.

The sequence for human TGF-$\beta$ was determined by direct amino acid sequence analysis and by deduction from the TGF-$\beta$ cDNA. The sequence of the different TGF-$\beta_1$ peptides obtained by clostripain digestion is in agreement with the cDNA sequence, except for a few residues which presumably are due to incorrect amino acid assignment in sequencing. The 112 amino acid TGF-$\beta$ sequence contains 9 cysteines, whereas the rest of the precursor contains only two (FIGS. 1b and 5). Previous studies have shown that reduction of the TGF-$\beta_1$ dimer of 25 kd results in the generation of two polypeptide chains of 12.5 kd[15]. Sequence analysis of the TGF-$\beta$ amino-terminus and of the TGF-$\beta_1$ peptides obtained after clostripain digestion strongly suggest that the TGF-$\beta$ dimer consists of two identical polypeptides. This homodimeric nature is also supported by the presence of only a single hybridizing DNA fragment upon Southern hybridization of human genomic DNA with a TGF-$\beta$ exon probe. Chou-Fasman man analysis[50] of the secondary structure shows that the TGF-$\beta$ polypeptide has an extensive $\beta$-sheet character with little, if any, $\beta$-helicity. The region immediately preceding the basic dipeptide cleavage site is likely in an α-helical configuration.

For purposes herein, preTGF-β is defined as the normal TGF-β precursor depicted in FIGS. 1b and 5 as well as other precursor forms of TGF-β in which the presequence is not that normally associated with TGF-β. These latter forms are to be considered insertional mutants of DNA encoding mature TGF-β. These mutants ordinarily comprise a presequence which is heterologous to TGF-β in the form of a fusion with mature TGF-β. The heterologous presequences preferably are obtained from other secreted proteins, for example pregrowth hormone, preproinsulin, viral envelope proteins, interferons and yeast or bacterial presequences recognized by mammalian host cells. The sequences for these secretory leaders are known, as are suitable sources for DNA encoding same if it is not desired to synthesize the DNA in vitro. They are linked to DNA encoding mature TGF-β by restriction enzyme digestion of the DNA containing the desired signal and the preTGF-β DNA. Synthetic oligonucleotides are prepared in order to introduce unique restriction sites (linkers) and, if necessary, DNA fragments needed to complete any presequence and mature TGF-β coding regions removed during restriction enzyme digestion. The synthesized linkers and/or fragments then are ligated to the restriction enzyme digest fragments containing the substitute signal and TGF-β coding region and inserted into a cloning vector and the vector is used to transform bacterial hosts. The mutant presequence thereafter is cloned into an expression vector and used to transform host cells. An illustrative example employing a viral envelope protein presequence is described below.

Optimally, DNA encoding the complete heterologous presequence is linked to the first codon of TGF-β DNA. Alternatively, DNA encoding the mature TGF-β coding sequence is ligated to DNA encoding the complete heterologous presequence plus a short portion, e.g. 21 to 45 base pairs, encoding the mature heterologous protein; this will result in the secretion of a fusion peptide on proteins which is useful as an immunogen or which can be cleaved to yield mature TGF-β (for example, by insertion of a collagenase cleavage site between the N-terminus of TGF-β and the C-terminus of the heterologous protein fragment). The objective of these constructions is to substitute a high efficiency secretory system for the native TGF-β secretory leader. However, it is by no means necessary to secrete TGF-β in order to produce it in recombinant culture.

Other deletion-insertion mutants include linking mature TGF-β species to viral proteins expressed in large intracellular quantities, e.g. retroviral core proteins, large T antigen from SV40 and the like, or to immunogenic bacterial proteins or polypeptides such as chemotactic polypeptides, in particular the potent chemotactic tripeptide Met-Leu-Phe-.

Expressed variants of preTGF-β, mature TGF-β or fragments thereof will exhibit amino acid sequences that gradually depart from the FIGS. 1b or 5 sequences as the number and scope of insertions, deletions and substitutions increases. This departure is measured as a reduction in homology between preTGF-β and the variant. All proteins or polypeptides that display TGF-β anchorage independent growth-promoting biological activity are included within the scope of this invention, regardless of the degree of homology that they show to the FIG. 1 protein. The reason for this is that some regions of preTGF-β. e g the presequence, are readily mutated, or even completely deleted as in the case of mature TGF-β, and thus biological activity will be retained. On the other hand, deletion of the nine cysteine residues (and accompanying disulfide linkages) in the mature TGF-β molecule will have a substantial adverse impact on this biological activity and in all likelihood would completely abrogate biological activity. In addition, a substitution mutant may exhibit full TGF-β growth-promoting activity and yet be less homologous if residues containing functionally similar amino acid side chains are substituted. Functionally similar refers to dominant characteristics of the side chains such as hydrophobic, basic, neutral or acidic, or the presence or absence of steric bulk. Thus the degree of homology that a given polypeptide bears to preTGF-β is not the principal measure of its identity as TGF-β. However, as a general guide, proteins or polypeptides that share at least some biological activity with mature TGF-β from natural sources and which are substantially homologous with the FIG. 1b sequence are to be considered as falling within the scope of the term TGF-β, e.g., TGF-β variants being about from 40 percent to 100 percent homologous with preTGF-β or any fragment thereof greater than about 20 residues, including variants having an amino acid sequence greater than about 75 percent homologous with the mature TGF-$\beta_1$ sequence. With respect to neoplastic cell growth-inhibiting activity. TGF-β excludes polypeptides known heretofore to exert such growth inhibitory activity, e.g. interferons tumor necrosis factor and lymphotoxin, but otherwise need not necessarily have homologous regions with the FIG. 1b sequences.

More narrow and specific factors in establishing the identity of a polypeptide as TGF-β are (a) the ability of antisera which are capable of substantially neutralizing the growth inhibitory or the anchorage independent growth promoting activity of mature TGF-β also to substantially neutralize the activity of the polypeptide in question, or (b) the ability of the candidate polypeptide to compete with TGF-β for a TGF-β cell surface receptor. However, it will be recognized that immunological identity and growth promoting identity are not necessarily coextensive A neutralizing antibody for the mature TGF-β of FIG. 1b may not bind a candidate protein because the neutralizing antibody happens to not be directed to a site on TGF-β that is critical for its growth promoting activity. Instead, the antibody may bind an innocuous region and exert its neutralizing effect by steric hindrance. Therefore, a candidate protein mutated in this innocuous region might no longer bind the neutralizing antibody, but it would nonetheless be TGF-β in terms of substantial homology and biological activity.

The TGF-β residues which are subject to site-directed mutagenesis for the preparation of variants which are likely to be antagonists to biologically active TGF-β are the cysteine residues. $Arg_{18}$, $Lys_{19}$, $Leu_{20}$, $Tyr_{21}$, $Ile_{22}$, $Phe_{24}$, $Leu_{28}$, $Gly_{29}$, $Trp_{30}$, $Trp_{32}$, $Ile_{33}$, $Pro_{36}$, $Gly_{38}$, $Tyr_{39}$, $Asn_{42}$, $Gly_{46}$, $Pro_{49}$, $Leu_{62}$, $Tyr_{65}$, $Pro_{70}$, $Va_{179}$, $Pro_{80}$, $Leu_{83}$, $Leu_{86}$, $Ile_{89}$, $Va_{190}$, $Tyr_{91}$, $Tyr_{92}$, $Leu_{102}$, $Asn_{105}$, $Met_{106}$, $Ile_{107}$ and $Val_{108}$. Substitutions which are made at these residues generally will be non-conserved. i.e. the substituted residue (a) differs substantially in hydrophobicity, for example a hydrophobic residue (Val, Ile, Leu, Phe or Met) substituted for a hydrophilic residue such as Arg,. Lys, Trp or Asn, or a hydrophilic residue such as Thr, Ser, His, Gln, Asn, Lys, Asp, Glu or Trp substituted for a hydrophobic residue; (b) differs substantially in its effect on polypeptide backbone orientation such as substitution of or for Pro or Gly by another residue; (c) differs substantially in electric charge, for example substitution of a negatively charged residue such as Glu or Asp for a positively charged residue such as Lys, His or Arg (and vice versa); or (d) differs substantially in steric bulk, for example substitution of a bulky residue such as His, Trp, Phe or Tyr for one having a minor side chain, e.g. Ala, Gly or Ser (and vice versa). Each of the foregoing target residues also is deleted (preferably in pairs) or non-conserved residues (also preferably in pairs) are inserted adjacent to the target residues. Ordinarily, only one residue at a time is subject to introduction of sequence variation. The regions for investigation of site-directed variation are residues 105.112, 77.95, and 20.49.

Identification of antagonists is routine. The candidate is incubated together with an equimolar amount of TGF-β otherwise detectable in the EGF-potentiated anchorage independent target cell growth assay[81], and the culture observed for failure to induce anchorage independent growth.

Antagonists that remain immunologically cross-reactive with native TGF-β are useful in immunoassays as standards or, when labelled, as reagents in competitive-type assays. Antagonists also are useful in therapy, e.g. of TGF-β dependent tumors.

The same residues targeted for site-directed variation in the generation of candidate antagonists also are targeted for the generation of agonists. Here, however, the variant residues which are substituted or inserted are conserved, i e., members of each class, e.g. hydrophobic, electronegative and the like as described above, are substituted for one another or inserted adjacent to a member of the same class, again preferably in pairs.

Also within the scope of this invention are TGF-β variants representing fusions of one TGF-β allele or sub-type with another, for example a C-terminal domain from TGF-$\beta_1$ having the homologous N-terminal domain substituted from TGF-$\beta_3$, or substitutional variants in which a domain from one allele or subtype is substituted for the homologous region from another allele or subtype.

It is important to observe that characteristics such as molecular weight and the like for the native or wild type mature TGF-β of FIG. 1*b* obtained from placenta or platelets are descriptive only for the native species of TGF-β. The variants contemplated herein may modify the characteristics of native TGF-β considerably, and this in fact may be the objective of the mutagenesis as is more fully described below. While TGF-β as defined herein includes native TGF-$\beta_1$, other related biologically active polypeptides will fall within the definition TGF-β species like the insertion mutants, deletion mutants, or fusion proteins described above will bring the mutant outside of the molecular weight established for native TGF-β. For example, fusion proteins with mature TGF-β or preTGF-β itself will have a greater molecular weight than native, mature TGF-β, while deletion mutants of mature TGF-β will have a lower molecular weight. Similarly, TGF-β is engineered in order to introduce glycosylation sites, thereby resulting in glycosylated TGF-β, or to substitute serine for post-translational processing of human preTGF-β in cell lines derived from nonprimate mammals may produce microheterogeneity in the amino terminal region of mature TGF-β, so that alanine will no longer be the amino terminal amino acid.

Note that the language "capable" of inducing anchorage independent growth in the definition for biological activity means that the preTGF-β or fragments thereof include polypeptides which can be converted, as by enzymatic digestion, to a polypeptide fragment which exhibits the desired biological activity. Typically, inactive precursors will be fusion proteins in which mature TGF-β is linked by a peptide bond at its carboxyl terminus to an insoluble or gelatinous protein. The sequence at or within the region of this peptide bond is selected so as to be susceptible to proteolytic hydrolysis whereby TGF-β is released, either in vivo for in situ generation or, as part of a manufacturing protocol, in vitro.

While TGF-β ordinarily means human TGF-β, TGF-β from sources such as murine, porcine, equine or bovine is included within the definition of TGF-β so long as it otherwise meets the standards described above for biological activity. TGF-β is not species specific, e.g., murine and human TGF-β are both effective in inducing anchorage independent growth of the same cell line. Therefore, TGF-β from one species can be used in therapy of another species. DNA encoding the TGF-β of other species is obtained by probing cDNA or genomic libraries from such species with labelled human preTGF-β cDNA.

Derivatives of TGF-β are included within the scope of this invention, Derivatives include glycosylated and covalent or aggregative conjugates with other TGF-β molecules, dimers or unrelated chemical moieties. Covalent derivatives are prepared by linkage of functionalities to groups which are found in the TGF-β amino acid chains or at the N- or C-termini, by means known in the art. These derivatives may, for example, include: aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative derivatives are useful as reagents in immunoassay or for affinity purification procedures. For example. TGF-β is insolubilized by covalent bonding to cyanogen bromide-activated Sepharose by methods known per se or adsorbed to polyolefin surfaces (with or without glutaraldehyde cross-linking) for use in the assay or purification of anti-TGF-β antibodies or cell surface receptors. TGF-β also is labelled with a detectable group, e.g., radioiodinated by the chloramine T procedure, covalently bound to rare earth chelates or conjugated to another fluorescent moiety for use in diagnostic assays, especially for diagnosis of TGF-β levels in biological samples by competitive-type immunoassays.

TGF-β variants generally are made by predetermined, i.e. site specific, methods. The objective of site specific mutagenesis is to construct DNA that encodes TGF-β as defined above. i.e., TGF0β which exhibits biological activity.

While the mutation site is predetermined, it is unnecessary that the mutation per se be predetermined. For example, in order to optimize the performance of the mutants at a given position random mutagenesis is conducted at the target codon and the expressed TGF-β variants are screened for optimal activity. Techniques are well known for making substitution variants at predetermined sites in DNA having a known sequence, for example M13 primer mutagenesis.

TGF-β mutagenesis is conducted by making amino acid insertions, usually on the order of about from 1 to 5 amino acid residues, or deletions of about from 1 to 10 residues. Substitutions, deletions, insertions or any subcombination may be combined to arrive at a final construct. As noted above, insertions include amino or carboxyl-terminal fusions, e.g. with a hydrophobic or immunogenic protein. The mutations in the DNA encoding such mutations should not ultimately place the sequence out of reading frame in an expression vector whereby the resulting protein is not biologically active TGF-β. The mutations also preferably will not create complementary regions that could produce translation-suppressing secondary mRNA structure.

Included herein are heterodimers of TGF-β. These typically include dimers in which one TGF-β chain is from one subclass, e.g. TGF-$\beta_1$, while the other is from another subclass, e.g. TGF-$\beta_3$. Similarly, TGF-β amino acid sequence variants are produced as homodimers or heterodimers with other amino acid sequence variants or with native TGF-β sequences. Heterodimers include dimers containing a first TGF-β sequence that is biologically active when present in a homodimer and a second TGF-β sequence that is not biologically active. Such heterodimers may be active as TGF-β antagonists. Heterodimers are readily produced by cotransforming host cells with DNA encoding the TGF-β chains selected. A proportion of the TGF-β so produced is expressed as the desired heterodimer, and transformants are screened for those which produce the greatest proportion of heterodimer.

DNA which encodes TGF-β is obtained by chemical synthesis, by screening reverse transcripts of mRNA from placental or other cells or by screening genomic libraries from eukaryotic cells. This DNA need not use the codons set forth in FIGS. 1*b* or 4*a*–4*c* so long as the host cell recognizes the codons which are used. DNA of this sort is as easily manufactured in vitro as the DNA of FIGS. 1*b* or 4*a*–4*c*. Also useful herein is nucleic acid, either RNA or DNA, which does not encode TGF-β thereof as defined herein but which nonetheless is capable of hybridizing with such DNA or RNA. Noncoding but hybridizing nucleic acid, while not used in the recombinant synthesis of TGF-β, is useful as an intermediate for making labelled probes in diagnostic assays for TGF-β mRNA or genomic DNA in test cells.

Diagnostic nucleic acid is covalently labelled with a detectable substance such as a fluorescent group, a radioactive atom or a chemiluminescent group by methods known per se. It is then used in conventional Southern or Northern hybridization assays. Such assays are employed in identifying TGF-β vectors and transformants as described in the Examples infra, or for in vitro diagnosis such as detection of TGF-β mRNA in tissues as a measure of mitogenic activity.

TGF-β is synthesized herein in host cells transformed with vectors containing DNA encoding TGF-β. A vector is a replicable nucleic acid construct. Vectors are used either to amplify and/or to express DNA which encodes TGF-β, or to amplify DNA that hybridizes with DNA or RNA encoding TGF-β. An expression vector is a replicable DNA construct in which a DNA sequence encoding TGF-β is operably linked to suitable control sequences capable of effecting the expression of TGF-β in a suitable host. Such control sequences include a transcriptional promoter, an optional operator sequence to control transcription, a sequence encoding suitable mRNA ribosomal binding sites, and sequences which control termination of transcription and translation. For expression of TGF-β in eukaryotic cells the vector also should include DNA encoding a selection gene. However, the selection gene can be supplied by an unlinked plasmid in cotransformation.

Vectors comprise plasmids, viruses (including phage), and integratable DNA fragments i.e., fragments that are integratable into the host genome by recombination. In the present specification, the vector is a plasmid in the sense that it is cloned in bacterial cells, but it integrates into the host cell genome upon cotransformation. However, all other forms of vectors which serve an equivalent function and which are, or become, known in the art are suitable for use herein. Suitable vectors will contain replicon and control sequences which are derived from species compatible with the intended expression host.

DNA regions are operably linked when they are functionally related to each other For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Cultures of cells derived from multicellular organisms are the preferred host cells herein. In principle, any higher eukaryotic cell culture is workable, whether from vertebrate or invertebrate culture. However, interest has been greatest in invertebrate cells, and propagation of vertebrate cells in culture per se has become a routine procedure in recent years [*Tissue Culture*, Academic Press, Kruse and Patterson, editors (1973)]. Examples of useful host cell lines are VERO and HeLa cells. Chinese hamster ovary (CHO) cell lines, and WI38, BHK, COS,7, 293 and MDCK cell lines.

Many eukaryotic cells are known to synthesize endogenous TGF-β. Thus, many potential host cells synthesize TGF-β of the host species. This TGF-β therefore is present in the TGF-β produced by transcription and translation of the transforming DNA. For example, hamster TGF-β is present in transformed CHO cells, and thus is present in cell extracts containing human TGF-β harvested from such cells While this is not necessarily disadvantageous because animal and human TGF-β is active across species lines, it is desirable to select a host/vector system that secretes as little of the endogenous animal TGF-β as possible. This is accomplished by (a) selecting host animal cell lines that synthesize low levels of animal TGF-β. (b) transforming the animal cell line with a vector for high efficiency TGF-β secretion (described above) and recovering human TGF-β from the culture medium or (c) transforming a human cell line, whereby any endogenous hTGF-$\beta$ that is produced would not be a contaminant.

It may be desirable to use a host cell line that is differentiated to synthesize endogenous TGF-$\beta$. Examples include megakaryoblast, promegakaryocytic or basophilic megakaryocytic cell lines. If suitable cell lines are not available they may be produced by EBV immortalization of megakaryoblasts, promegakaryocytes or basophilic megakaryocytes recovered from mammalian bone marrow. The TGF-$\beta$ of the desired species is recovered from transformant cell cultures by immunoaffinity chromatography using antibodies specific for host TGF-$\beta$.

Expression vectors for such cells ordinarily include an origin of replication (for extrachromosomal amplification), a promoter located upstream from the TGF-$\beta$ coding sequences, along with an enhancer if desired, RNA splice site (if intron-containing TGF-$\beta$-encoding genomic DNA is used), and a transcriptional termination sequence including a polyadenylation site located 3' to the TGF-$\beta$ sequence.

The transcriptional and translational control sequences in expression vectors to be used in transforming vertebrate cells preferably are provided from viral sources. For example, commonly used promoters are derived from polyoma. Adenovirus 2, and most preferably Simian Virus 40 (SV40). The early and late promoters of SV40 are particularly useful because both are obtained easily from the virus as a fragment which also contains the SV40 viral origin of replication[54]. Smaller or larger SV40 fragments may also be used, provided the approximately 250 bp sequence extending from the Hind III site toward the Bgl I site located in the viral origin of replication is included. Since TGF-$\beta$ appears to be toxic to mammalian cell transformants and thus may interfere with attempts to amplify the gene, yields may be improved by the use of inducible promoters, e.g. the metallothionein promoter, Drosophila heat shock promoter or mouse mammary tumor virus promoter. Further, it is also possible to utilize the TGF-$\beta$ genomic promoter, control and/or signal sequences normally associated with TGF-$\beta$, provided such control sequences are compatible with and recognized by the host cell. If TGF-$\beta$ untranslated regions are included in expression vectors, yields may be improved by substituting A or T bases for G or C bases immediately 5' to the start codon and deleting G-C rich domains in the 3' untranslated sequences of the cDNA.

An origin of replication may be provided either by construction of the vector to include an exogenous origin, such as may be derived from SV40 or other viral (e g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by cotransformation with a selectable marker and the TGF-$\beta$ DNA. An example of a suitable selectable marker is dihydrofolate reductase (DHFR) or thymidine kinase. Such markers are proteins, generally enzymes that enable the identification of transformant cells, i.e., cells which had been competent to take up exogenous DNA. Generally, identification is by survival of transformants in culture medium that is toxic or from which the cells cannot obtain critical nutrition without having taken up the marker protein In selecting a preferred host mammalian cell for transfection by vectors which comprise DNA sequences encoding both TGF-$\beta$ and DHFR, it is appropriate to select the host according to the type of DHFR protein employed If wild type DHFR protein is employed, it is preferable to select a host cell which is deficient in DHFR thus permitting the use of the DHFR, coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin[55].

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line. CHO-KI (ATCC No. CCL 61). Alternatively, DHFR+ host cells are used by cotransforming the cells with DNA encoding the neomycin resistance gene, DHFR and TGF-$\beta$. The initial transfections are screened for neomycin resistance, and resistant transformants then amplified on MTX.

Other methods suitable for adaptation to the synthesis of TGF-$\beta$ in recombinant vertebrate cell culture are described in Gething et al.[56], Mantei et al.[57], and Levinson et al.[58,59].

TGF-$\beta$ is recovered from lysed, transformed cells and insoluble cell debris separated by centrifugation. Alternatively, the culture supernatants from transformed cells that secrete TGF-$\beta$ are simply separated from the cells by centrifugation. Then the TGF-$\beta$ generally is purified by methods known in the art[15,16,17] using gel filtration in the presence of acid followed by HPLC and elution on an acetonitrile gradient. However, such methods are not necessarily required to prepare a therapeutic product.

As a further or substitute purification step, cell lysates or supernatants are heated for a period and at a temperature sufficient to denature and precipitate contaminant proteins but not TGF-$\beta$; TGF-$\beta$ is a remarkably heat stable protein, perhaps as a result of extensive disulfide bond formation. As a result, the heating should be conducted in a medium that contains low amounts of disulfide reagents such as dithiothreitol or the like. Heating also is combined with acidification since TGF-$\beta$ is known to be stable to 1M acetic acid.

Mature, native TGF-$\beta$ is not glycosylated. Therefore it is separated from any residual contaminant heat, and acid-stable glycoproteins by adsorbing the glycoproteins on lectin columns such as lentil lectin-linked sepharose. This step, less desirably, can go before the heat and acid treatment. TGF-$\beta$ will elute with the unadsorbed fraction. The recombinant TGF-$\beta$ is recovered from host cells expressing endogenous TGF-$\beta$ (or undesired homodimers) by transforming the host cells with a TGF-$\beta$ variant which is glycosylated by the host The sugar "tag" enables the recombinant TGF-$\beta$ to be recovered free of endogenous TGF-$\beta$ by lectin affinity chromatography, elution of the glycosylated TGF-$\beta$ and removal, if desired, of the sugar residues by conventional enzymatic digestion.

If high purity product is desired the crude or partially purified mixture thereafter is subjected to chromatofocusing.

TGF-$\beta$ is prepared for administration by mixing TGF-$\beta$ at the desired degree of purity with physiologically acceptable carriers, i.e., carriers which are nontoxic to recipients at the dosages and concentrations employed. Ordinarily, this will entail combining TGF-$\beta$ with buffers, antioxidants such as ascorbic acid, low molecular weight (less than about 10 residues) polypeptides, proteins, amino acids, carbohydrates including glucose or dextrins, chelating agents such as EDTA, and other excipients. TGF-$\beta$ for use in therapeutic administration must be sterile. This is readily accomplished by filtration through sterile filtration (0.2 micron) membranes. TGF-$\beta$ ordinarily will be stored as an aqueous solution since it is highly stable to thermal and oxidative denaturation.

TGF-$\beta$ optionally is combined with activating agents such as TGF-$\alpha$ or EGF species as is described further in U.S. Ser. No. 500,833, now abandoned, and is administered in accord with said application.

Various therapeutic indications for TGF-$\beta$ compositions are known.

The first, and preferred, indication is topical application to incisions or exposed tissue for the promotion of wound healing. There are no limitations as to the type of wound or other traumata that can be treated, and these include (but are not limited to): first, second and third degree burns (especially second and third degree); epidermal and internal surgical incisions, including those of cosmetic surgery; wounds, including lacerations, incisions, and penetrations; and epidermal ulcers including decubital (bed-sores), diabetic, dental, hemophiliac, and varicose. Doses such as those previously described for wound healing[17] will be suitable as starting doses in these indications.

TGF-$\beta$ compositions are applied to burns in the form of a sterile irrigant, preferably in combination with a physiological saline solution, or in the form of ointments or suspensions, preferably in combination with purified collagen. The compositions also may be impregnated into transdermal patches, plasters, and bandages, preferably in a liquid or semi-liquid form. Autonomicrobial agents such as silver sulfadiazine should be included in such articles or compositions. Debridement agents such as proteolytic enzymes also can be included if they do not hydrolyze TGF-$\beta$ or a hydrolysis-resistant TGF-$\beta$ mutant is employed.

TGF-$\beta$ also is administered systemically for the treatment of wounds and similar traumata. Systemic administration is useful provided that there are no, or limited, undesirable side-effects, such as the stimulation of neoplastic cellular growth in patients with cancer. TGF-$\beta$ compositions for systemic administration preferably are formulated as sterile, isotonic parenteral injections or infusions.

The amount of activating agent (such as TGF-$\alpha$, EGF or other growth factors) administered with TGF-$\beta$ depends directly upon the amount of TGF-$\beta$ present in the activated compositions as administered to the recipient, the growth factors selected and the clinical status of the patient.

Initial dosing of TGF-$\beta$ should be delivered to the therapeutic site in a concentration of about from 0.1 to 150 ng/ml and thereafter adjusted in line with clinical experience. Since TGF-$\beta$ compositions both provoke and sustain cellular regeneration, a continual application or periodic reapplication of the compositions is indicated. The clinician will be expected to modify the dosage in accordance with clinical experience.

In order to simplify the Examples certain frequently occurring methods will be referenced by shorthand phrases.

Plasmids are designated by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the site for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 $\mu$g of plasmid or DNA fragment is used with about 2 units of enzyme in about 20 $\mu$l of buffer solution. Appropriate buffers and substrate amounts for particular restriction enzymes are specified by the manufacturer Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional[85].

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally[86,87].

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern[68], and hybridization as described by T. Maniatis et al.[88].

"Transformation" means introducing DNA into an organism so that the DNA is replicable, either as an extrachromosomal element or chromosomal integrant. Unless otherwise provided, the method used herein for transformation of E. coli is the CaCl$_2$ method of Mandel et al.[89].

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id., p. 90, may be used.

"Oligonucleotides" are short length single or double stranded polydeoxynucleotides which are chemically synthesized by known methods and then purified on polyacrylamide gels.

All citations are expressly incorporated by reference.

EXAMPLE 1

Purification and Sequence Analysis of Human TGF-β

The known purification method of Assoian et al.[15] was scaled up and modified to obtain enough homogeneously pure human TGF-β$_1$ for amino acid sequencing. 250 units of human platelets were extracted in a Waring blender with 1 liter of acid-ethanol. Addition of 4 liters of ether gave rise to a precipitate which was collected by vacuum filtration over Whatman No 1 paper. The precipitate was dissolved overnight in 50 ml of 1M acetic acid and purified by gel filtration on a Biogel P-60 column (10×100 cm), equilibrated in 1M acetic acid. The fractions containing TGF-β$_1$ were identified by analytical SDS-polyacrylamide gel electrophoresis and bioassay[15]. Peak fractions were pooled, freeze-dried and redissolved in 20 ml 1M acetic acid, 8M urea. Subsequent gel filtration over a Biogel P-60 column (5×90 cm) in 1M acetic acid, 8M urea yielded about 50 percent pure TGF-β. These peak fractions were then diluted with 1 volume of water and applied to a semipreparative RPP C18 (Synchropak) HPLC column in 0.1 percent trifluoroacetic acid and eluted with a 20-50 percent acetonitrile gradient. The TGF-β$_1$ thus obtained was quantitated by amino acid analysis, showing a yield of about 0.5 mg per preparation. Denaturing SDS-polyacrylamide gel electrophoresis was performed as described[60]. In agreement with previous work the non-reduced TGF-β$_1$ migrated as a 25 kD protein in a SDS-polyacrylamide gel, while reduction with β-mercaptoethanol converted it into a 12.5 kD species. This suggested that TGF-β consists of two 12.5 kD polypeptide chains linked by intermolecular disulfide bridges[15].

In order to obtain protein sequence information, the purified TGF-β$_1$ was reduced, alkylated and subjected to amino-terminal sequence analysis. 1.2 nmole of TGF-β was dialyzed into 8M urea and reduced by incubation in 0.1M Tris-HCl (pH 8 5), 10 mM dithiothreitol, 8M urea. Subsequent alkylation took place in the presence of 50 mM iodoacetate at room temperature in the dark. This reaction was terminated after 30 min. by addition of an excess β-mercaptoethanol and dialysis. 0.7 nmole of this TGF-β$_1$ was used for the direct NH$_2$-terminal sequence analysis. 1.2 nmole of reduced and alkylated TGF-β$_1$ was digested in 0.75 M urea, 50 mM NH$_4$HCO$_3$, 5 mM dithiothreitol for 24 hours with 1 percent clostripain[15]. An additional 1 percent of clostripain was added after 12 hours reaction time. The reaction products were separated on a Synchropak RPP C18 reverse phase column (4.6×250 mm) with a 0-70 percent acetonitrile gradient in 0.1 percent trifluoroacetic acid. Sequence determination took place using either an extensively modified Beckman 890C spinning cup sequencer[61] or a vapor phase sequencer as described by Hewick et al.[62]. (Applied Biosystems, model 470A), with amino acid derivative identification by reversed phase HPLC on a Rainin Microsorb C-8 column. The amino acid sequence of several peptides was determined. One of these fragments was the NH$_2$-terminal segment, while another large peptide yielded a 37 amino acid sequence which overlapped the NH$_2$-terminal sequence and established 60 residues of contiguous sequence.

Unmodified TGF-β$_1$ was also treated with CNBr. Cleavage at the methionine residue resulted in the complete loss of biological activity, documenting that at least part of this C-terminal octapeptide is needed for biological activity (data not shown).

EXAMPLE 2

Isolation of a TGF-β Exon

The approach we followed for the initial identification of a nucleotide sequence encoding TGF-β$_1$ adopted the "long probe" strategy used previously for TGF-α[7]. Long oligonucleotides designed on the basis of the partial protein sequence were used as hybridization probes for the identification of TGF-β$_1$ exon in a human genomic DNA library. The TGF-β$_1$ exon was then used as a probe for the isolation of TGF-β$_1$ cDNAs.

Two 44-base-long deoxyoligonucleotides, βLP1 and βLP2, complementary to sequences coding for amino acids 3 to 17 and 30 to 44, respectively, were chemically synthesized[63, 64]. The choice of nucleotide sequence was based upon the codon bias observed in human mRNAs[26]. CpG dinucleotides, which are relatively rare in vertebrate DNA[27], were avoided whenever possible. In addition, sixteen 14-mers were synthesized which are complementary to all possible codons for amino acids 13 to 17. These deoxyoligonucleotides and the corresponding amino acid sequence are shown below.

NH$_2$—AlaLeuAsp Thr Asn Tyr Cys Phe Ser Ser Thr Glu Lys Asn Cys Cys ValArgGluLeuTyr

CTGTGGTTGATAACGAAGAGGAGGTGTCTCTTCTTGACGACGCA 5'

TT$^C_T$TT$^G_A$AC$^G_A$AC$^G_A$CA

LeuGlyTrp Lys Trp Ile His Glu Pro Lys Gly Tyr His Ala Asn Phe CysLeuGlyProCysProTyr

ACCTTCACCTAGGTACTCGGTTTCCCGATAGTACGGTTGAAGAC 5'

The nucleotides marked with a dot are bases for which there is no ambiguity in the codon.

A human genomic DNA library[28] was screened under low stringency hybridization conditions using $^{32}$P-labelled βLP-1 as probe. Approximately 7.5×10$^5$ recombinant phage from a human genomic fetal liver library[28] were hybridized using low stringency conditions[65] with the $^{32}$P-labelled 44-mer βLP-1 after replica plating onto nitrocellulose filters[66]. DNA was prepared from 58 of the hybridizing phage and hybridized with the $^{32}$P-labelled βLP-1 and βLP-2 oligonucleotides using the "dot blot" analysis method[67] and Southern hybridization[68] of BamHI digestion mixtures. The two phage DNAs which hybridized with both oligonucleotides were digested and probed with the pool of $^{32}$P-labelled 14-mers again by Southern hybridization. 14-mer hybridizations were performed at 37° C. in 6 xSSC. 0.5 percent NP40, 6 mM EDTA. 1X Denhardt's solution and 50 µg/ml salmon sperm DNA. Several washes were performed at room temperature in 6xSSC before autoradiography. DNA from phage βλ58 hybridized with the oligonucleotides βLP-1, βLP-2 and with the 14-mer pool. The sequences hybridizing to βLP-2 and the 14-mers were localized within the same 4.2 kbp BamHI fragment, while probe βLP-1 hybridized to a 20 kbp BamHI fragment. The hybridizing BamHI fragments were subcloned into pBR322. The nucleotide sequence of smaller hybridizing fragments was determined by dideoxynucleotide chain termination method[69] after subcloning into M13 derivatives[70].

The screening of the genomic DNA library resulted in the isolation of an exon coding the part of the TGF-β$_1$ coding sequence starting at mature residue 10. In order to obtain the entire TGF-β$_1$ coding sequence, this exon was used as a probe to screen a λgt10 based cDNA library derived from human term placenta mRNA.

EXAMPLE 3

Isolation of TGF-β cDNAs

Total RNA was extracted[71] from the different cell sources and the polyadenylated mRNA fraction was isolated by oligo(dT)-cellulose chromatography[72]. The cDNA was prepared[73] by priming with dT$_{12-18}$ or the deoxyoligonucleotide ACACGGGTTCAGGTAC. The double-stranded cDNA was treated with nuclease S1 (Miles Laboratories) followed by E. coli DNA polymerase I Klenow fragment (Boehringer Mannheim) and subcloned into EcoRI cleaved λgt10 as described[74], except that asymmetric EcoRI linkers[75] were used, thus avoiding the need for the EcoRI methylase treatment. The recombinant phage were plated on E. coli C600 Hfl[74] and replica plated onto nitrocellulose filters[66]. These were hybridized with $^{32}$P-labelled[76] restriction fragments of the Example 2 exon at 42° C. in 50 percent formamide. 5 x SSC, 50 mM sodium phosphate pH 6.8, 0.1 percent sodium pyrophosphate, 5 x Denhardt s solution, 50 µg/ml salmon sperm DNA and washed in 0.2 x SSC, 0.1 percent SDS at the same temperature Low stringency hybridization conditions[65] were used in the case of the $^{32}$P-labelled deoxyoligonucleotides. The nucleotide sequence of the TGF-β$_1$ cDNA restriction fragments was determined by the dideoxyoligonucleotide chain termination method[69] after subcloning into M13 phage derivatives[70]. The cDNAs obtained are schematically shown in FIG. 1a. λβCl was isolated from a human placenta cDNA library using the genomic exon (FIG. 3) as probe. The screening of approximately 750,000 oligo-dT primed placenta cDNA clones resulted in the isolation of one TGF-β cDNA (λβCl) of about 1.050 bp. The previously determined partial TGF-β$_1$ sequence established the reading frame and revealed the sequence coding for the complete TGF-β$_1$ polypeptide. This sequence begins with the NH$_2$-terminal alanine residue and is followed 112 codons later by a stop codon, only 20 base pairs from the 3' end. The λβCl EcoRI cDNA insert was used in turn to screen the A172 glioblastoma cDNA library leading to the isolation of λβC3.19. Screening of a specifically primed HT1080 fibrosarcoma cDNA library with the 32P-labelled KonI-KpnI and the upstream EcoRI-KonI fragment of the λβC3.19 cDNA insert yielded λβC4.10, 4.33 and 4.37. Another similar library was screened with the λβC4–33 insert and a synthetic 40-mer corresponding to nucleotides 1.40, leading to the isolation of λβC5.7b.

Since none of more than seventy TGF-β cDNAs isolated from different oligo(dT)-primed cDNA libraries contained more than a few nucleotides of 3' untranslated region, the 3' untranslated sequence was determined using cloned genomic DNA Hybridization analysis showed that the 3' end of the λβCl cDNA insert was present in the genomic DNA phage βλ58. DNA sequence analysis revealed the presence of an exon coding for the carboxy terminal part of TGF-β$_1$, followed by the stop codon and the 3' untranslated end (FIG. 1b). An AATAAA hexanucleotide sequence[32] was encountered 500 bp downstream from the termination codon, thus permitting an assignment of the putative polyadenylation site. Assuming this is indeed the polyadenylation signal, the calculated size of TGF-β$_1$ mRNA is in close agreement with the 2.3 to 2.5 kb length determined from the Northern hybridization experiments (Example 4). Additional screening of oligo(dT)-primed placenta and HT1080 cDNA libraries using the genomic DNA probe for the 3' untranslated end did not identify a single hybridizing cDNA phage.

EXAMPLE 4

Diacnostic Method Using TGF-β cDNA Probes

Polyadenylated RNA was recovered from the hepatoma HEP-G2, Wilms tumor TuWi, glioblastoma A172, bladder carcinoma T24, squamous epidermoid carcinoma A431, mammary carcinoma MCF-7, nasopharyngeal carcinoma KB, fibrosarcoma HT1080, Burkitt lymphoma B-lymphoblasts Daudi and Raji, T-lymphoblast Molt-4. Peripheral blood lymphocytes (PBLs) were prepared and mitogen-induced with staphylococcal enterotoxin B and phorbol myristate as described[53]. RNA was harvested in this case after 24 hours. 4 µg of polyadenylated mRNA was electrophoresed into formaldehyde-1.2 percent agarose gel[29] and blotted onto nitrocellulose filters[30] The $^{32}$P-labelled76 EcoRI cDNA insert of λβCl was used as probe under high stringency conditions used above. Comparison with the position of the 28S and 18S rRNA on the gel suggests a length of 2.3-2.5 kb for the TGF-β mRNA. In some cases a smaller mRNA species may be present, although partial degradation of the mRNA cannot be excluded.

TGF-β mRNA was detectable in all human tumor cell lines including tumor cells of neuroectodermal origin, such as TuWi (Wilms Tumor) and A172 (glioblastoma), and the carcinoma cell lines T24 bladder carcinoma. A431 (squamous epidermoid carcinoma), MCF-7 (mammary carcinoma) and KB (nasopharyngeal carcinoma). HT1080, a fibrosarcoma derived cell line, which we had chosen as a source of mRNA for the cDNA cloning, contained relatively high levels of TGF-β mRNA TGF-β mRNA was not only present in cell lines derived from solid tumors of meso-, endo- and ectoblastic origin, but was also detectable in tumor cell lines of hematopoietic origin, e.g. Daudi (Burkitt lymphoma B-lymphoblast), Raji (Burkitt lymphoma B-lymphoblast), and Molt-4 (T-cell leukemia). The presence of TGF-$\beta$ mRNA is not restricted to tumor cells, since it is clearly detectable in placenta and peripheral blood lymphocyte (PBL) mRNA. Strikingly, the level of TGF-$\beta$ mRNA is significantly elevated after mitogenic stimulation of PBLs. TGF-$\beta$ mRNA was not detectable in human liver, yet was present in the HEP-G2 hepatoma cell line. In all cases, the TGF-$\beta$ mRNA migrated as a species of an apparent length of 2.3 to 2.5 kbases. In some cases a smaller mRNA species of about 1.8 to 1.9 kb may be present, although this could be due to partial degradation of the mRNA.

EXAMPLE 5

Recombinant Synthesis of TGF-$\beta$

The plasmid used for recombinant synthesis of TGF-$\beta_1$ was pMBTE6. The following prophetic method for making this plasmid is preferred over the more complex method actually employed in its construction.

p342E[79] is digested with EcoRI, blunted with E. coli DNA polymerase I (Klenow fragment) and the four dNTPs, digested with SalI and Fragment 1 (containing the Amp$^r$ gene of pBR322) recovered.

p342E is simultaneously digested with SalI and HindIII and the HBsAg-encoding fragment is recovered as Fragment 2.

Finally, the SV40 genome is simultaneously digested with HindIII and HincII, and the 596 bp fragment containing the SV40 origin and early promoter recovered as Fragment 3.

Fragments 1, 2 and 3 are ligated in a three way ligation and the ligation mixture is transformed into E. coli strain 294 (ATCC 31446). The transformed culture is plated on ampicillin media plates and resistant colonies are selected. p342E-blunt was recovered from a transformant colony.

p342E blunt is digested simultaneously with HindIII and EcoRI and the large vector fragment recovered. This fragment is ligated to a polylinker having the following sequence

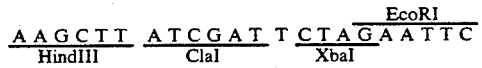

and the ligation mixture used to transform E. coli ATCC 31446 as described above. pCVSV-HBs is recovered from an ampicillin-resistant transformant.

pCVSV-HBs is digested with HindIII and EcoRI simultaneously and the vector fragment isolated (the 18 bp HindIII-EcoRI fragment will not appear in the gel due to its small size).

pgD-DHFR-Trunc (European Patent Application 84.305909.8), a plasmid containing DNA encoding the herpes simplex gD protein, is simultaneously digested with StuI and HindIII and the approximately 760 bp fragment recovered which contains DNA encoding the herpes simplex signal peptide and the coding region for the N-terminal part of the mature HSV-1gD protein Plasmid pJ2.9 from European Patent Application 84.305909.8 can be used in the same fashion.

p$\beta$Cl (FIG. 1a) is digested with SmaI and BamHI, and the 480 bp fragment recovered. This fragment contains most of the sequence coding for preTGF-$\beta_1$ including the sequence coding for the N-terminus of mature TGF-$\beta_1$ through residue 314.

p$\beta$Cl is digested with BamHI and EcoRI and the 270 bp fragment recovered These two separate digestions of p$\beta$Cl aliquots were conducted because the BamHI-EcoRI p$\beta$Cl fragment contains a SmaI site. The 270 bp fragment contains the sequence coding for the rest of the TGF-$\beta_1$ molecule and extends 20 bp beyond the stop codon.

The pCVSV-HBs vector fragment is ligated in a four way ligation with the foregoing 760, 270 and 480 bp fragments. The resulting construction (pCVSVgD) thus contained a hybrid coding sequence (Herpes simplex gD-1 signal peptide and part of the gD-1 envelope protein linked in frame to the preTGF-$\beta_1$ precursor fragment) under the control of the SV40 early promoter. This hybrid coding sequence is in turn followed by the 3' untranslated sequence and the polyadenylation signal of the hepatitis surface antigen.

pCVSVgD is digested with EcoRI, blunted with Klenow and the four dNTPs, and thereafter digested with PstI. Two fragments are so obtained, with the fragment including the hybrid coding sequence and the SV40 promoter (fragment A) being recovered.

pCVSVgD is digested with BamHI, blunted with Klenow and the four dNTPs, and thereafter digested with PstI. Four fragments are obtained after these digestions. The fragment containing the pBR322 origin and Ampr gene (about 1900 bp) is recovered as Fragment B.

Fragments A and B are ligated and the ligation mixture used to transform E. coli ATCC 31.446. Plasmid pMBTE6 is recovered from an Amp$^r$ colony.

Plasmid pMBTE6 was transfected into DHFR deficient CHO cells[55] together with plasmid pFD1190. The latter plasmid encodes DHFR, thereby conferring methotrexate resistance on the transfected cells and allowing for selection of TGF-$\beta$ expressing transformants. Any DHFR$^-$ mammalian host cell is suitable for use. Alternatively, one can use any mammalian host cell, cotransform the host cell with a plasmid encoding neomycin resistance, and identify transformants by their ability to grow in neomycin-containing medium.

The transfected CHO cells were selected by culturing in HGT$^-$ medium. The cells were allowed to grow to confluency in 15 cm diameter plates. The cells thereafter were cultured in serum-free medium for 48 hours prior to harvest. The culture medium was decanted from the plates and assayed in a soft agar assay for the presence of TGF-$\beta$ as described[78].

50 ml supernatant medium was lyophilized and dissolved in 700 $\mu$l 4mM HCl-0.1 percent bovine serum albumin. 200 $\mu$l of this solution and of serial three-fold dilutions were assayed. The number of colonies in soft agar with a diameter of >89 $\mu$m were counted. The maximal response (plateau-value) obtained in the presence of saturating levels of TGF-$\beta_1$ was about 1500 per plate. Less than 50 colonies were obtained in the absence of TGF-$\beta_1$. A half maximal response was obtained with a 9-fold dilution of the sample derived from the cells transformed with a negative control plasmid. Calculations from the values obtained by serial dilution of the MBTE6 supernatant showed that the half maximal value was obtained at a 70-fold dilution.

The assays of serial dilutions show that cells transformed with MBTE6 and pFD11 synthesize about 8–10 times more TGF-$\beta_1$ per ml of medium than do CHO cells transfected with pFD11 alone or with pFD11 together with a control plasmid (one which was similar to pMBTE6 except that the Herpes coding sequence is replaced by the sequence coding for the bacterial STII signal peptide), even prior to subcloning and selection in MTX-containing media. This additional amount of TGF-$\beta$ is human TGF-$\beta_1$.

Since biologically active TGF-$\beta_1$ is found in the culture medium it is concluded that CHO cells cleave preTGF-$\beta$ in the same fashion as do human cells in vivo to secrete mature native TGF-$\beta$. This conclusion is very much strengthened by the fact that the slope of the TGF-$\beta_1$ concentration dilution curve in the soft agar is identical for both the endogenous natural TGF-$\beta_1$ and the recombinant TGF-$\beta_1$, thus reflecting a similar if not identical affinity for the TGF-$\beta$ receptor.

EXAMPLE 6

Isolation of DNA Encoding TGF-$\beta_3$ $1.5 \times 10^6$ plaques from porcine ovarian cDNA library screened under low hybridizing conditions with the $^{32}$P-labelled *E. coli* insert of $\lambda\beta$Cl (1050bp) in pH6.8 hybridization buffer containing 5xSSC. 20% formamide. 5xDenhardts, 0.1% Na-pyrophosphate, 0.05M NaPO$_4$, 0.1% SDS and 50 $\mu$g/ml salmon sperm DNA at 42° C. overnight. Washes were in 2xSSC at 37° C. Phage was purified from positively hybridizing plaques and their DNA inserts were sequenced. The approximately 200 positively hybridizing cDNA inserts fell into three classes: Porcine TGF-$\beta_1$ (2 plaques), G-C rich cDNAs which did not encode a TGF-$\beta$ polypeptide (6) and $\lambda$11.3, a gene fragment which contained DNA encoding porcine TGF-$\beta_3$ downstream from mature residue 10.

Figure 4A:
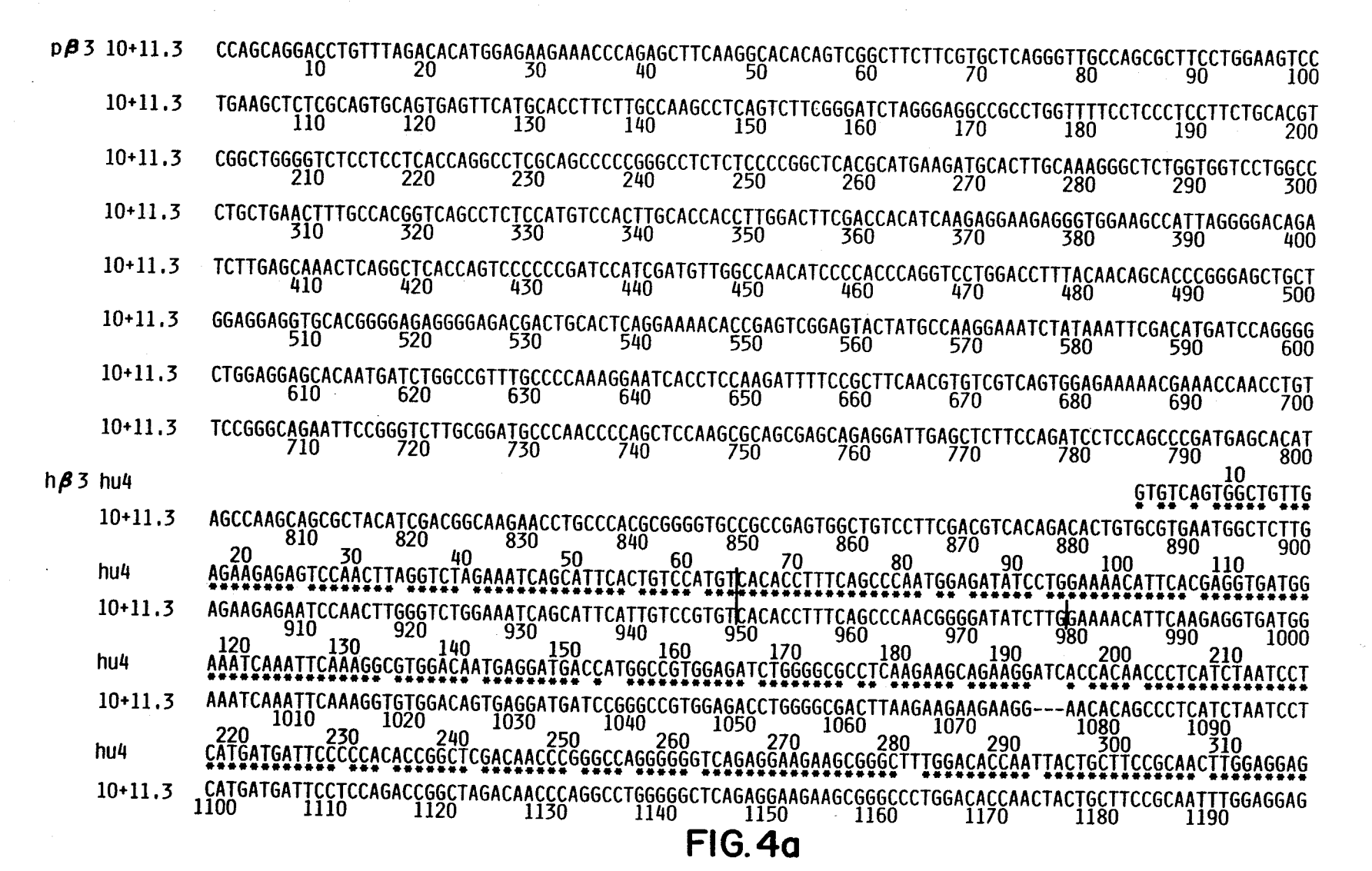
Figure 4B:
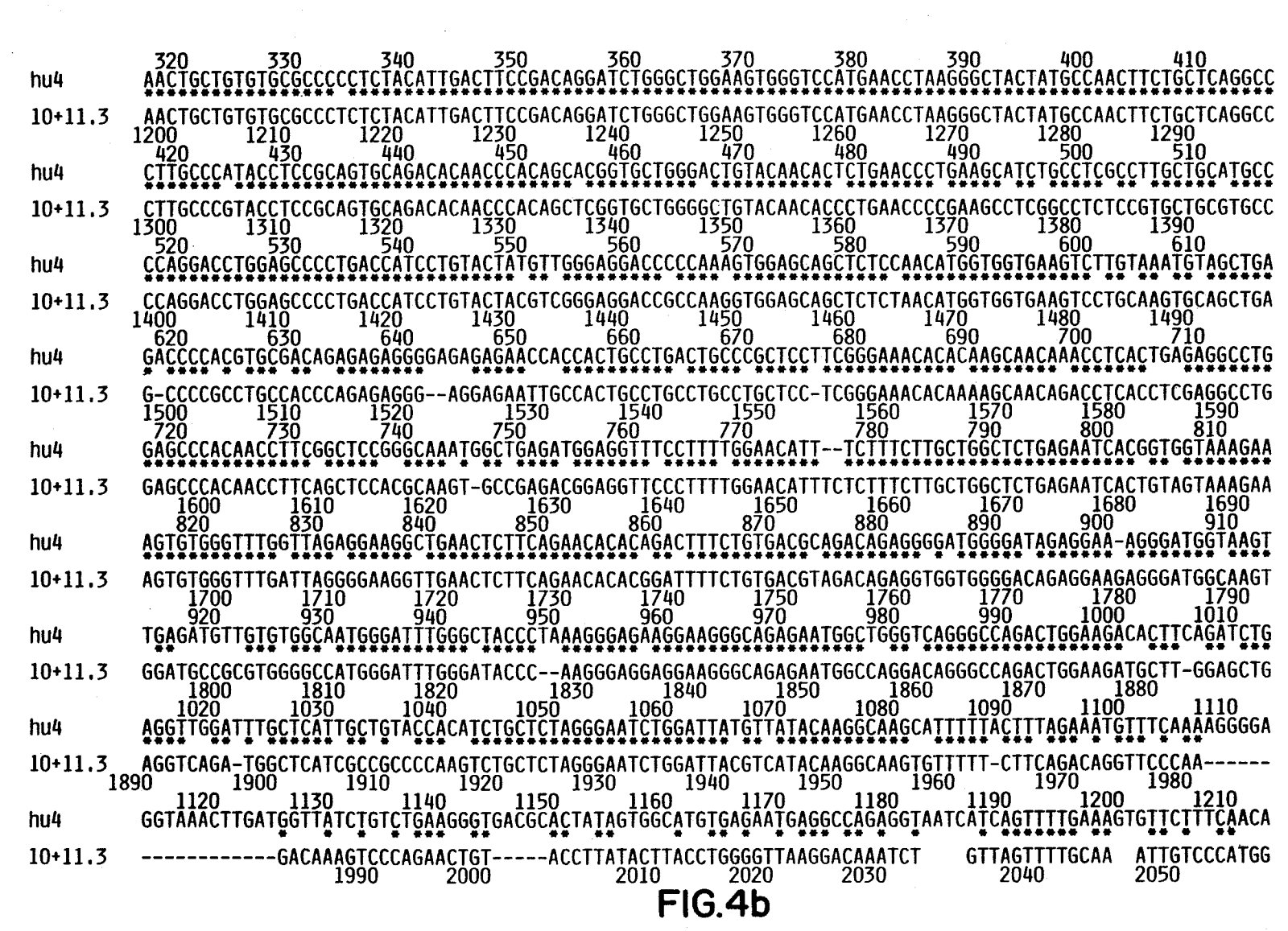
Figure 4C:
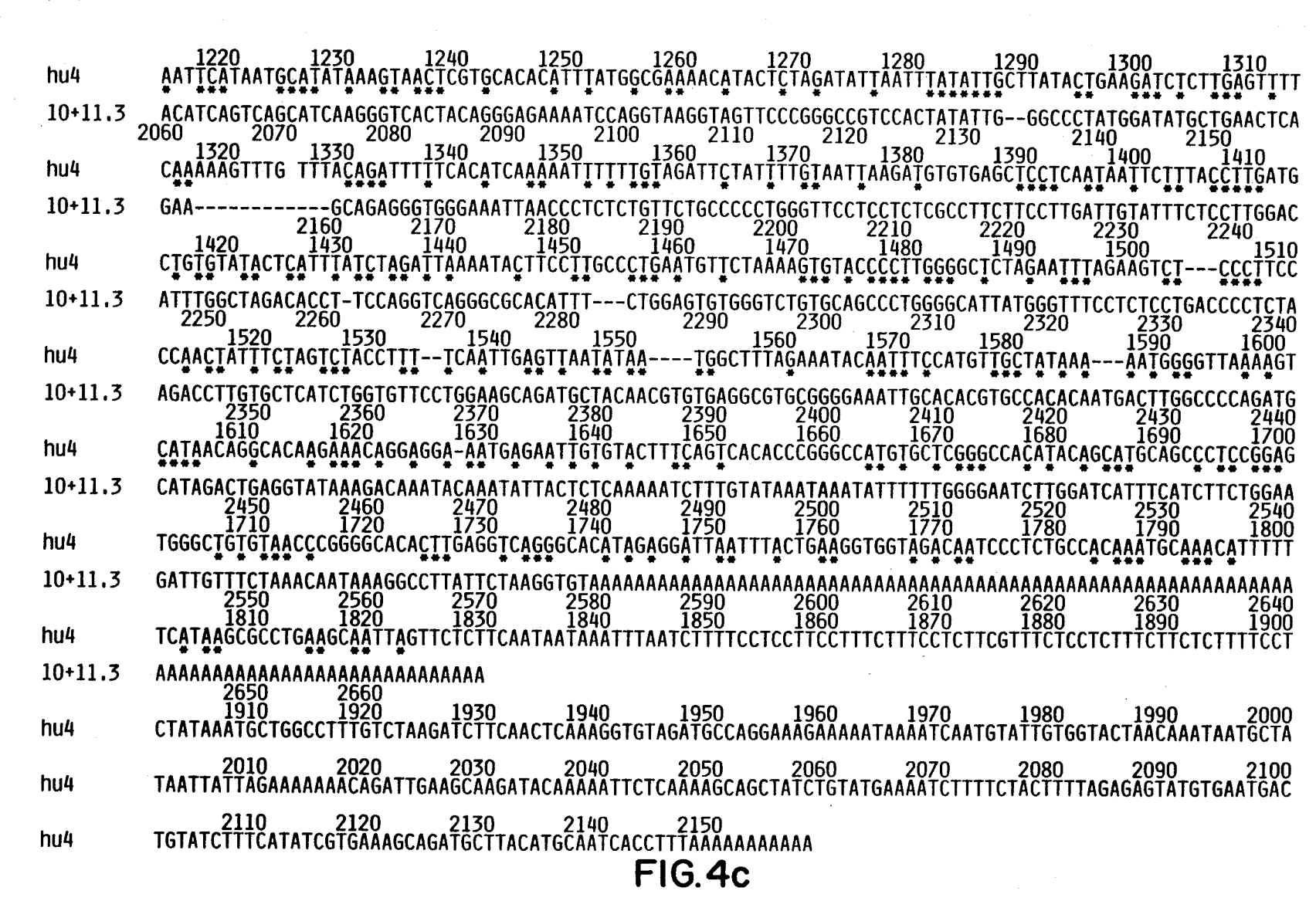

The labelled EcoRI insert of $\lambda$11.3 was used under high stringency conditions (as above but 50% formamide, and with washes using 0.1 xSSC at 42° C.) to rescreen $1 \times 10^6$ plaques from a porcine ovarian cDNA $\lambda$ library. Of 20 positively hybridizing plaques, one ($\lambda$10) contained the entire porcine TGF-$\beta_3$ sequence. The combined nucleotide and imputed amino acid sequences encoded by $\lambda$10+11.3 are shown in FIGS. 4a–4c.

$1 \times 10^6$ plaques from a human ovarian cDNA library were screened with labelled porcine cDNA. One positive plaque ($\lambda$hu4) was identified. $\lambda$hu4 has the nucleotide and imputed amino acid sequence set forth in FIGS. 4a–4c. FIG. 5 is a comparison of the amino acid sequences imputed from the porcine and human TGF-$\beta_3$ cDNAs. The candidate start codons for the porcine precursors are boxed.

TGF-$\beta_3$ is expressed in recombinant cell culture and recovered therefrom in substantially the same way as TGF-$\beta_1$, making allowances for departures in nucleotide and amino acid sequence as will be apparent to those skilled in the art. Since the complete precursor for human TGF-$\beta_3$ is not disclosed, in order to express human TGF-$\beta_3$ it will be desirable to reprobe genomic or cDNA libraries for DNA encoding the remaining N-terminal precursor sequence, or ligate DNA encoding the available human sequence (starting at the codon for residue 3) with the DNA encoding the porcine TGF-$\beta_3$ precursor through residue 297 (numbered as shown in FIG. 5), or prepare DNA encoding a heterologous mammalian or viral signal fusion with DNA encoding mature human TGF-$\beta_3$.

BIBLIOGRAPHY

1. De Larco, J. E., et al., Proc Natl. Acad. Sci. USA 75: 4001–4005 (1978).
2. Roberts, A. B et al., Fed. Proc. 42: 2621.2625 (1983).
3. Todaro, G. J. et al., Proc. Natl. Acad. Sci. USA 77: 5258–5262 (1980).
4. Marquardt, H. et al., Science 223: 1079–1082 (1984).
5. Roberts, A. B. et al., Proc. Natl. Acad Sci. USA 77: 3494–3498 (1980).
6. Ozanne, B. et al., J. Cell Physiol. 105: 163–180 (1980).
7. Derynck, R. et al., Cell 38:287–297 (1984).
8. Lee, D. C. et al., Nature 313: 489–491 (1985).
9. Linsley, P. S. et al., Proc. Natl. Acad. Sci USA 82:356–360 (1985).
10. Roberts, A. B. et al. Proc Natl. Acad. Sci. USA 78: 5339–5343 (1981).
11. Roberts, A. B. et al., Nature 295: 417–419 (1982).
12. Roberts, A. B. et al., Biochemistry 22:5692-5698 (1983).
13. Frolik, C. A. et al., Proc. Natl. Acad. Sci. USA 80:3637–3680 (1983).
14. Childs, C. B. et al., Proc Natl Acad Sci USA 79:5312–5316 (1982).
15. Assoian, R. K. et al., J. Biol. Chem. 258:7155–7160 (1983).
16. Assoian, R. K. et al., Nature 309:804–806 (1984).
17. Sporn, M. B. et al., Science 219:1329–1331 (1983).
18. Frolik, C. A. et al. J. Biol. Chem. 259: 10995–11000 (1984).
19. Tucker, R. F., et al., Proc. Natl. Acad. Sci. USA 81:6757–6761 (1984).
20. Assoian, R. K. et al., Cell 36: 35–41 (1984).
21. Tucker, R. F. et al., Cancer Res. 43:1581–1586 (1983).
22. Anzano, M. A. et al., Molec Cell. Biology 5:242–247 (1985).
23. Roberts, A. B. et al., Proc. Natl. Acad. Sci. USA 82:119–123 (1985).
24. Tucker, R. F. et al., Science 226:705–707 (1984).
25. Mitchell, W. M. Meth. Enzymol. XLVII, p. 165–170 (1977).
26. Grantham, R. et al., Nucl. Acids Res. 9:43-73 (1981).
27. Bird, A. P . Nucl. Acids Res. 8:1499–1504 (1980).
28. Lawn, R. M. et al., Cell 15:1157–1174 (1978).
29. Dobner, P. R. et al., Proc. Natl. Acad. Sci. USA 78:2230–2234 (1981).
30. Thomas, P. S., Proc. Natl. Acad. Sci. USA 77:5201–5205 (1980).
31. Volckaert, G. et al., Gene 15:215–223 (1981).
32. Proudfoot, N. J. et al., Nature 253:211–214 (1976).
33. Levy, W. P. et al., Proc. Natl. Acad. Sci. USA 78:6186–6190 (1981).
34. Renderknecht, E. et al., J. Biol. Chem. 259:6790–6797 (1984).
35. No citation.
36. No citation.
37. Battey, J. et al., Cell 34:779–787 (1983).
38. McGrogan, M. et al., J. Biol. Chem. 260(4):2307–2314 (1985).
39. Valerio, D. et al., EMBO J. 5(1):113–119 (1986).
40. McKnight, S. L. et al., Cell 37:253–262 (1984).
41. Dynan, W. S. et al., Cell 35:79–87 (1983).
42. Gidoni, D. et al., Nature 312:409–413 (1984).
43. Benoist, C. et al., Nucl. Acids Res. 127–142 (1980).
44. Noda, M. et al., Nature 295:202–206 (1982).
45 Gubler, U. et al., Nature 295:206–208 (1982).

46. Amara, S. G, et al., Nature 298:240-244 (1982).
47. Nakanishi, S. et al., Nature 278:423-427 (1979).
48. Kyte, J. et al., J. Mol. Biol. 157:105-132 (1982).
49. Winzler, R. J. in Hormonal Proteins and Peptides 1 (Li, C.I., ed.) (New York, Academic Press) p. 1.15 (1973).
50. Garnier. J. et al., J. Mol. Biol. 120:97-120 (1978).
51. No citation.
52. No citation.
53. No citation.
54. Fiers et al., "Nature". 273:113 (1978).
55. Urlaub and Chasin "Proc. Natl. Acad. Sci. USA" 77:4216-4220 (1980).
56. Gething. M. J. et al.. "Nature" 293:620-625 (1981).
57. N. Mantei et al., "Nature" 281:40-46 (1981).
58. A. Levinson et al., EP 117.060A.
59. A. Levinson et al., EP 117,058A.
60. Laemmli, U. K., Nature 227:680-685 (1970).
61. Rodriguezm H. et al , Anal. Biochem. 140:538-547 (1984).
62. Hewick, R. M. et al.. J Biol. Chem. 256:7990-7997 (1981).
63. Crea, R. et al., Nucl. Acids Res. 8:2331-2348 (1980).
64. Beaucage, S. L. et al., Tetrahedron Lett. 22:1859 (1981).
65. Ullrich, A. et al., EMBO J. 3:361-364 (1984).
66. Benton, W. D. et al., Science 196:180-182 (1977).
67. Kafatos, F. C. et al., Nucl. Acids Res. 7:1541-1552 (1979).
68. Southern, E. M., J. Mol. Biol. 98:503-517 (1975).
69. Sanger, F. et al., Proc. Natl. Acad. Sci. USA 74:5463-5467 (1977).
70. Messing, J. et al., Nucl. Acids Res. 9:309-321 (1981).
71. Ullrich, A. et al., Science 196:1313-1317 (1977).
72. Aviv, H. et al., Proc. Natl. Acad. Sci. USA 69:1408-1412 (1972).
73. Wickens, M. P. et al . J. Biol. Chem. 253:2483-2495 (1978).
74. Huynch, T. V. et al., in DNA Cloning Techniques, A Practical Approach (Glover, D., ed.) (IRL, Oxford).
75. Norris, K. E. et al.. Gene 7:355-362 (1979).
76. Taylor, J. M. et al. Biochim. Biophys. Acta 442:324-330 (1976).
77. Crowley et al., Molec. Cell. Biol. 3:44-55 (1983).
78. Anzano et al., Molec. Cell. Biol. 5:242-247 (1985).
79. EP 73.656A.
80. Seyedin et al , J. Biol. Chem. 262(5):1946-1949 (1987).
81. Ying et al., Biochem. Biophys. Res. Commun. 135 950-956 (1986).
82. Mason et al., Nature 318:659-663 (1985).
83. Fuller et al., J. Clin. Endocrin. Metab. 54:1051-1055 (1982).
84. Fuller et al., Gynecol. Oncol. 17:124-132.
85. T. Maniatis et al., *Molecular Cloning A Laboratory Manual* (New York: Cold Spring Harbor Laboratory, 1982) pp. 133-134.
86. R. Lawn et al., "Nucleic Acids Res." 9:6103-6114 (1981).
87. D. Goeddel et al., "Nucleic Acids Res.: 8:4057 (1980).
88. T. Maniatis et al., "Cell" 15:687-701 (1978).
89. Mandel et al . "J. Mol Biol " 53: 154 (1970).
90. Simonsen and Levinson, "Proc. Natl. Acad. Sci. USA 80: 2495-2499 (1983).
91. Derynck et al., "Cancer Res." 47:707-712 (1987).
92. Bringman et al., "Cell" 48:429-440 (1987).

We claim:

1. A method comprising (a) constructing a vector which includes nucleic acid encoding TGF-$\beta$, (b) transforming a host eukaryotic cell with the vector, (c) culturing the transformed cell and (d) recovering TFG-$\beta$ from the culture.

2. The method of claim 1 wherein the eukaryotic cell is a Chinese hamster ovary cell line.

3. The method of claim 1 wherein the TGF-$\beta$ is preTGF-$\beta$.

4. The method of claim 1 where the TGF-$\beta$ has the amino acid sequence of human TGF-$\beta$.

5. The method of claim 1 wherein the TGF-$\beta$ is a polypeptide having a viral secretory signal sequence at its N-terminus and the sequence of mature TGF-$\beta$ at its C-terminus.

6. The method of claim 5 wherein the nucleic acid encoding the fusion polypeptide is operatively linked to a viral promoter.

7. The method of claim 5 wherein the nucleic acid encoding the fusion polypeptide is operably linked to an unducible promoter.

8. A method comprising a(a) constructing a vector that includes nuclic acid encoding TGF-⊕1, (b) transforming a host eukaryotic cell with the vector, (c) culturing the transformed cell, and (d) recovering TGF-$\beta$1 from the culture.

9. The method of claim 8 wherein the eukaryotic cell is a Chinese hamster ovary cell line.

10. The method of claim 8 wherein the TGF-$\beta$1 is preTGF-⊕1.

11. The method of claim 8 wherein the TGF-$\beta$1 has the amino acid sequence of human TGF-$\beta$1.

12. The method of claim 8 wherein the TGF-$\beta$1 is a fusion polypeptide having a viral secretory signal sequence at its N-terminus and the sequence of mature TGF-$\beta$1 at its C-terminus.

13. The method of claim 12 wherein the nucleic acid encoding the fusion polypeptide is operably linked to viral promoter.

14. The method of claim 12 wherein the nucleic acid encoding the fusion polypeptide operably linked to an inducible promoter.

15. A method comprising (a) constructing a vector that includes nucleic acid encoding TGF-$\beta$3, (b) transforming a host eukaryotic cell with the vector, (c) culturing the transformed cell, and (d) recovering TGF-$\beta$3 from the culture.

16. The method of claim 15 wherein the eukaryotic cell is a Chinese hamster ovary cell line.

17. The method of claim 15 wherein the TGF-$\beta$3 is preTGF-$\beta$3.

18. The method of claim 15 wherein the TGF-$\beta$3 has the amino acid sequence of human TGF-$\beta$3.

19. The method of claim 15 wherein the TGF-$\beta$3 is a fusion polypeptide having a viral secretory signal sequence at its N-terminus and the sequence of mature TGF-$\beta$3 at its C-terminus.

20. The method of claim 19 wherein the nucleic acid encoding the fusion polypeptide is operably linked to a viral promoter.

21. The method of claim 19 wherein the nucleic acid encoding the fusion polypeptide is operably linked to an inducible promoter.

* * * * *

UNITED STATES PATENT AND TRADEMARK OFFICE
CERTIFICATE OF CORRECTION

PATENT NO. : 5,168,051

DATED : Dec. 1, 1992

INVENTOR(S) : Rik M.A. Derynck and David V. Goeddel

It is certified that error appears in the above-identified patent and that said Letters Patent is hereby corrected as shown below:

In the title, part [54], on the face of the patent add --AND-- after "TGF-$\beta$".

In column 1, in the title, add --AND- after "TGF-$\beta$".

In column 20, line 37, replace "Diacnostic" with --Diagnostic--

In column 26, line 7, claim 1, replace "TFG" with --TGF--.

In column 26, line 15, claim 5, add --fusion-- after "is a".

In column 26, line 24, claim 7, replace "unducible" with --inducible--.

In column 26, line 25, claim 8, delete "a" after "comprising".

In column 26, line 26, claim 8, replace "nuclic" with --nucleic--.

In column 26, line 26, claim 8, replace "TGF-$\oplus$" with --TGF-$\beta$--.

In column 26, line 33, claim 10, replace "TGF-$\oplus$" with --TGF-$\beta$--.

UNITED STATES PATENT AND TRADEMARK OFFICE
CERTIFICATE OF CORRECTION

Page 2 of 2

PATENT NO. : 5,168,051

DATED : December 1, 1992

INVENTOR(S) : Rik M.A. Derynck and David V. Goeddel

It is certified that error appears in the above-identified patent and that said Letters Patent is hereby corrected as shown below:

In column 26, line 41, claim 13, add --a-- after "linked to".

In column 26, line 44, claim 14, add --is-- after "polypeptide".

Signed and Sealed this

Eleventh Day of July, 1995

*Attest:*

BRUCE LEHMAN

*Attesting Officer*   *Commissioner of Patents and Trademarks*